(12) United States Patent
Grosskreutz

(10) Patent No.: US 7,592,330 B2
(45) Date of Patent: Sep. 22, 2009

(54) METHODS AND COMPOSITIONS FOR PRESERVING THE VIABILITY OF PHOTORECEPTOR CELLS

(75) Inventor: Cynthia Lee Grosskreutz, Swampscott, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 11/500,171

(22) Filed: Aug. 7, 2006

(65) Prior Publication Data

US 2007/0032427 A1 Feb. 8, 2007

Related U.S. Application Data

(60) Provisional application No. 60/706,376, filed on Aug. 8, 2005, provisional application No. 60/773,898, filed on Feb. 16, 2006.

(51) Int. Cl.
*A61K 31/33* (2006.01)
(52) U.S. Cl. ...................................................... 514/183
(58) Field of Classification Search ........................ None
See application file for complete search history.

(56) References Cited

U.S. PATENT DOCUMENTS

| | | | |
|---|---|---|---|
| 5,444,042 A | 8/1995 | Bartus et al. | |
| 5,622,967 A | 4/1997 | Dolle et al. | |
| 5,667,968 A | 9/1997 | LaVail et al. | |
| 5,760,048 A | 6/1998 | Wang et al. | |
| 5,767,079 A | 6/1998 | Glaser et al. | |
| 5,840,719 A | 11/1998 | Rubin et al. | |
| 6,083,944 A | 7/2000 | Chatterjee et al. | |
| 6,100,267 A | 8/2000 | Daines et al. | |
| 6,180,402 B1 | 1/2001 | Granville et al. | |
| 6,245,523 B1 | 6/2001 | Altieri | |
| 6,303,579 B1 * | 10/2001 | Pang et al. | 514/19 |
| 6,316,465 B1 | 11/2001 | Pershadsingh et al. | |
| 6,384,073 B1 | 5/2002 | Sakuma et al. | |
| 6,465,464 B2 | 10/2002 | Wheeler et al. | |
| 6,534,693 B2 | 3/2003 | Fischell et al. | |
| 6,750,196 B1 | 6/2004 | Reh et al. | |
| 2002/0040015 A1 | 4/2002 | Miller et al. | |
| 2003/0104618 A1 * | 6/2003 | Hughes | 435/372 |
| 2004/0097425 A1 * | 5/2004 | Shima et al. | 514/19 |
| 2005/0129684 A1 | 6/2005 | Zacks et al. | |
| 2006/0073182 A1 * | 4/2006 | Wong et al. | 424/426 |
| 2007/0014760 A1 * | 1/2007 | Peyman | 424/85.1 |
| 2007/0032427 A1 | 2/2007 | Grosskreutz | |
| 2007/0287756 A1 | 12/2007 | Nakazawa | |

FOREIGN PATENT DOCUMENTS

| | | |
|---|---|---|
| WO | WO-9818485 | 5/1998 |
| WO | WO-0038703 | 7/2000 |
| WO | WO-0109327 | 2/2001 |
| WO | WO-03061519 | 7/2003 |
| WO | WO-2005/105133 | 11/2005 |
| WO | WO-2007/019427 | 2/2007 |
| WO | WO-2008/063639 | 5/2008 |

OTHER PUBLICATIONS

Friberg et al. (Serious retinal detachment resembling central serous chorioretinopathy following organ transplantation, Graefe's Arch Clin Exp Opthalmol, 1990, 228, 305-9).*
Laatikainen (Diffuse chronic retinal pigment epitheliopathy and exudative retinal detachment, Acta opthalmologica, 1994, 72, 533-6, abstract).*
Lai et al. (Cain, a Novel Physiologic Protein Inhibitor of Calcineurin, J. Biol. Chem., 1998. 273, 18325-18331).*
Kashishian et al. (AKAP79 Inhibits Calcineurin through a Site Distinct from the Immunophilin-binding Region, J. Biol. Chem., 1998, 273, 27412-27419).*
Garver et al. (Reduction of Calcineurin Activity in Brain by Antisense Oligonucleotides Leads to Persistent Phosphorylation of Protein at Thr181 and Thr231, Mol. Pharm., 1999, 55, 632-641).*
Adida et al. (1998) "Developmentally Regulated Expression of the Novel Cancer Anti-Apoptosis Gene Survivin in Human and Mouse Differentiation," Am. J. Pathol. 152(1): 43-49.
Afford et al. (2000) "Demystified . . . Apoptosis," J. Clin. Pathol. 53: 55-63.
Ambrosini et al. (1997) "A novel anti-apoptosis gene, survivin, expressed in cancer and lymphoma," Nat. Med. 3(8): 917-21.
Ambrosini et al. (1998) "Induction of Apoptosis and Inhibition of Cell Proliferation by survivin Gene Targeting," J. Biol. Chemistry 273(18): 11177-82.
Anderson et al. (1983) "Retinal Detachment in the Cat: The Pigment Epithelial-Photoreceptor Interface," Invest. Ophthalmol. Vis. Sci. 24: 906-926.
Angelastro et al. (2001) "Characterization of a novel isoform of caspase-9 that inhibits apoptosis," J. Biol. Chem. 276 (15): 12190-200.
Antonsson et al. (2000) "The Bcl-2 Protein Family," Experiment. Cell Res. 256: 50-57.
Asai et al (1999) "High level calcineurin activity predisposes neuronal cells to apoptosis," J Biol Chem 274(48):34450-8.

(Continued)

*Primary Examiner*—Cecilia Tsang
*Assistant Examiner*—Christina Bradley
(74) *Attorney, Agent, or Firm*—Goodwin Procter LLP

(57) ABSTRACT

Provided are methods and compositions for maintaining the viability of photoreceptor cells following retinal detachment. The viability of photoreceptor cells can be preserved by administering a neuroprotective agent, for example, a substance capable of suppressing endogenous calcineurin or constitutively active calcineurin, inhibiting cleavage of calcineurin to constitutively active calcineurin, and/or directly or indirectly antagonizing calcineurin or constitutively active calcineurin (and combinations thereof), to a mammal having an eye with retinal detachment. The neuroprotective agent maintains the viability of the photoreceptor cells until such time that the retina becomes reattached to the underlying retinal pigment epithelium and choroid. The treatment minimizes the loss of vision, which otherwise may occur as a result of retinal detachment.

7 Claims, 4 Drawing Sheets

OTHER PUBLICATIONS

Bamford et al. (2000) "Therapeutic Applications of Apoptosis Research," Experimental Cell Res. 256: 1-11.
Bretton et al. (2000) "Protein Complexes Activate Distinct Caspase Cascades in Death Receptor and Stress-Induced Apoptosis," Experim. Cell Res. 256: 27-33.
Calbiochem Catalog (1999), (4 pages).
Cao et al. (2001) "Intracellular Bax translocation after transient cerebral ischemia: Implications for a role of the mitochondrial apoptotic signaling pathway in ischemic neuronal death," J. Cer. Blood Flow Met. 21: 321-33.
Caspase-Inhibitors, from http://www.celldeath.de/encyclo/caspases/inhibito.htm, viewed Jan. 13, 2003 (2 pages).
Chang et al. (1995) "Apoptotic Photoreceptor Cell Death After Traumatic Retinal Detachment in Humans," Arch Ophthalmol. 113: 880-86.
Chen et al. (1996) "bcl-2 overexpression reduces apoptotic photoreceptor cell death in three different retinal degenerations," Proc Natl Acad Sci USA 93(14):7042-7.
Cook et al. (1995) "Apoptotic photoreceptor degeneration in experimental retinal detachment," Invest Ophthalmol Vis Sci. 36: 990-996.
Cross et al.(2000) "Serine/Threonine Protein Kinases and Apoptosis," Experiment. Cell Res. 256: 34-41.
Deveraux et al. (1998) "IAPs block apoptotic events induced by caspase-8 and cytochrome c by direct inhibition of distinct caspases.," EMBO Journal 17(8): 2215-23.
Donovan et al. (2001) "Light-induced photoreceptor apoptosis in vivo requires neuronal nitric-oxide synthase and guanylate cyclase activity and is caspase-3-independent," J. Biol. Chem. 276:23000-8.
Dunaief et al. (2002) "The role of apoptosis in age-related macular degeneration," Arch. Ophthalmol. 120: 1435-42.
Ekert et al. (1999) "Review: Caspase Inhibitors," Cell Death and Differentiation 6:1081-1086.
Hakem et al. (1998) "Differential requirement for caspase 9 in apoptotic pathways in vivo," Cell 94:339-352.
Harrison et al. (2001) "Caspase mRNA expression in a rat model of focal cerebral ischemia," Mol. Brain. Res. 89: 133-46.
He et al. (2000) "Lead and Calcium Produce Rod Photoreceptor Cell Apoptosis by Opening the Mitochondrial Permeability Transition Pore," J. of Biol. Chem. 275(16): 12175-12184.
Hengartner (2000) "The biochemistry of apoptosis," Nature 407: 770-.
Hisatomi et al. (2001) "Relocalization of Apoptosis-Inducing Factor in Photoreceptor Apoptosis Induced by Retinal Detachment in Vivo," Am. J. of Pathol. 158(4):1271-78.
Hisatomi et al. (2002) "Critical Role of photoreceptor apoptosis in functional damage after retinal detachment," Curr. Eye Res. 24(3): 161-172.
Hockenberry et al. (1993) "Bcl-2 functions in an antioxidant pathway to prevent apoptosis," Cell 75:241-251.
Huppertz et al. (1999) "The apoptosis cascade—morphological and immunohistochemical methods for its visualization," Anat. Embryol. 200:1-8.
Jomary et al. (2001) "Characterization of Cell Death Pathways in Murine Retinal Neurodegeneration Implicates Cytochrome c Release, Caspase Activation, and Bid Cleavage," Molec. Cell. Neurosci. 18: 335-46.
Kane et al. (1993) "Bcl-2 inhibition of neural death: decreased generation of reactive oxygen species." Science 262:1274-1277.
Kantrow et al. (2000) "Regulation of tumor necrosis factor cytotoxicity by calcineurin." FEBS Lett 483(2-3):119-24.
Katai et al. (1999) "Caspaselike Proteases Activated in Apoptotic Photoreceptors of Royal College of Surgeon Rats," Invest. Ophthalmol. Vis. Sci. 40(8): 1802-07.
Kerr et al. (1972) "Apoptosis: a basic biological phenomenon with wide-ranging implications in tissue kinetics," Br. J. Cancer 26:239-257.
Kroemer et al. (1997) "The proto-oncogene BcI-2 and its role in regulating apoptosis," Nat. Med. 3:614-620.
Krupinski et al. (2000) "Expression of caspases and their substrates in the rat model of focal cerebral ischemia," Neurobiol. Dis. 7: 332-42.
Kwong et al. (2000) "N-Methyl-D-Aspartate (NMDA) Induced Apoptosis in Adult Rabbit Retinas," Exp. Eye Res. 71: 437-44.
LaVail et al. (1998) "Protection of Mouse Photoreceptors by Survival Factors in Retinal Degenerations," Invest. Ophthalmol. Vis. Sci. 39(3): 592-602.
Liu et al. (1999) "Activation of Caspase-3 in the Retina of Transgenic Rats with the Rhodopsin Mutation S334ter during Photoceptor Degeneration," Jour. Neurosci. 19(12): 4778-4785.
Loeffler et al. (2000) "The Mitochondrion in Cell Death Control: Certainties and Incognita," Exp. Cell Res. 256: 19-26.
Love (2003) "Apoptosis and brain ischaemia," Prog. Neuropsychopharm Biol. Psych. 27: 267-82.
Lu et al. (2000) "Advances in Secondary Spinal Cord Injury," Spine 25(14) 1859-66.
Marc et al. (1998) "Amino Acid Signatures in the Detached Cat Retina," Invest. Ophthalmol. Vis. Sci. 39(9): 1694-702.
Nickells et al. (1996) "Apoptosis in ocular disease: a molecular overview," Ophthalmic Genetics 17(4): 145-65.
Nir et al. (2000) "Expression of BcI-2 protects against photoreceptor degeneration in retinal degeneration slow (rds) mice," J Neurosci 20(6):2150-4.
Oppenheim (1991) "Cell death during development of the nervous system," Ann. Rev. Neurosci. 14:453-501.
Ranger et al. (2001) "Mouse models of cell death," Nature Genetics 28: 113-18.
Reme et al. (1998) "Apoptotic Cell Death in Retinal Degenerations," Progress Retinal Eye Res. 17 (4): 443-64.
Singh et al. (2001) "Cell-specific caspase expression by different neuronal phenotypes in transient retinal ischemia," J. Neurochem. 77: 466-475.
Susin et al. (1999) "Molecular characterization of mitochondrial apoptosis-inducing factor," Nature 397: 441-46.
Tamm et al. (1998) "IAP-family protein survivin inhibits caspase activity and apoptosis induced by Fas (CD95), Bax, caspases, and anticancer drugs," Cancer Res. 58: 5315-20.
Veis et al. (1993) "BcI-2-deficient mice demonstrate fulminant lymphoid apoptosis, polycystic kidneys, and hypopigmented hair," Cell 75:229-240.
Walczak et al. (2000) "The CD95 (APO-1/Fas) and the TRAIL (APO-2L) Apoptosis Systems," Exp. Cell Res. 256: 58-66.
Walker et al. (1988) "Patterns of cell death," Meth. Achie. Exp. Pathol. 13:18-54.
Wilson et al. (1995) "Apoptosis as the Mechanism of Photoreceptor Cell Death in Experimental Retinal Detachment," Invest. Ophthamol. Vis. Sci. 36(4) Abstract of Poster Presentation #308-216.
Wyllie et al. (1980) "Cell death: the significance of apoptosis," Int. Rev. Cytology 68: 251-306.
Yang et al. (Feb. 2004) "Preventing Retinal Detachment-Associated Photoreceptor Cell Loss in Bax-Deficient Mice," Invest. Ophthalmol. .Vis. Sci. 45(2): 648-54.
Yuan et al. (2002) "Apoptosis in the nervous system," Nature 407(12): 802-809.
Zacks et al. (2003) "Caspase Activation in an Experimental Model of Retinal Detachment Invest," Ophthalmol. Vis. Sci. 44: 1262-1267.
Zheng et al. (2000) "Divinations and Surprises: Genetic Analysis of Caspase Function in Mice," Experiment. Cell Res. 256: 67-73.
Farkas et al. (2001) "Apoptosis, neuroprotection, and retinal ganglion cell death: an overview," Int. Opthalmol. Clinic. 41(1): 111-130.
Kroemer et al. (1995) "The biochemistry of programmed cell death," FASEB J. 9(13): 1277-1287.
Kroemer et al. (1997) "Mitochondrial control of apoptosis," Immunol. Today 18: 44-51.
Levin (1999) "Direct and indirect approaches to neuroprotective therapy of glaucomatous optic neuropathy," Survey Opthalmol. 43(Suppl.): S98-101.
Nickells (1996) "Retinal ganglion cell death in glaucoma: the how, the why, and the maybe," J. Glaucoma 5: 345-356.
Nickells et al. (1996) "Apoptosis of retinal ganglion cells in glaucoma: An update of the molecular pathways involved in cell death," Survey Ophthalmol. 43(Suppl.): S151-161.
Osborne et al. (1999) "Neuroprotection in relation to retinal ischemia and relevance to glaucoma," Survey Opthalmol. 43(Suppl.): S102-128.

Travis (1998) "Mechanisms of cell death in the inherited retinal degenerations," Am. J. Hum. Genet. 62(3): 503-508.

Zacks et al. (2004) "FAS-mediated apoptosis and its relation to intrinsic pathway activation in an experimental model of retinal detachment," Invest. Ophthalmol. Vis. Sci. 45(12): 4563-69.

Zacks et al. (2007) "Role of the FAS-signaling pathway in photoreceptor neuroprotection," Arch. Ophthalmol. 125(10): 1389-1395.

Aaberg TM. Does hyperoxygenation limit retinal degeneration after retinal detachment? Am J Ophthalmol. (1999) vol. 128(2):231.

Geller SF, Lewis GP, Fisher SK. FGFR1, signaling, and AP-1 expression after retinal detachment: reactive Wüller and RPE cells. Invest Ophthalmol Vis Sci. (2001) vol. 42(6):1363-1369.

Limb GA, Little BC, Meager A, Ogilvie JA, Wolstencroft RA, Franks WA, Chignell AH, Dumonde DC. Cytokines in proliferative vitreoretinopathy. Eye. 1991;5 ( Pt 6):686-693.

International Search Report for International Application No. PCT/US2005/013710, mailed on Dec 23, 2005.

Sobrin et al. (2004) "Pigment epithelial-derived factor (PEDF) inhibits apoptosis in a rat model of retinal detachment," The Aging Eye ARVO 2004 Annual Meeting, Program#/Poster#: 2064/B875.

Tezel G, Yang X, Yang J, Wax MB. Role of tumor necrosis factor receptor-1 in the death of retinal ganglion cells following optic nerve crush injury in mice. Brain Res. Jan. 23, 2004;996(2):202-212.

Cao et al. (1999) "Pigment epithelium-derived factor protects cultured retinal neurons against hydrogen peroxide-induced cell death," J Neurosci Res. 57: 789-900.

Cayouette et al. (1999) "Pigment epithelium-derived factor delays the death of photoreceptors in mouse models of inherited retinal degenerations," Neurobiol Dis. 6(6):523-32.

Ku et al. (1995) "Regulation of basic fibroblast growth factor (bFGF) gene and protein expression following its release from sublethally injured endothelial cells," J Cell Biochem. 58(3): 328-43.

Young et al. (2004) "Modulation of Apoptosis Following Combination PEDF and Photodynamic Therapy for Choroidal Neovascularization in the Rat Model," Invest Opthalmol Vis Sci. 45: E-Abstract 2231.

Almeida et al. (2004) "FK506 prevents mitochondrial-dependent apoptotic cell death induced by 3-nitropropionic acid in rat primary cortical cultures," Neurobiol Dis. 17: 435-444.

Axxora Platform Product No. ALX-260-014, for Calpeptin, available at, www.axxora.com (last visited Dec. 7, 2007, 2 pages).

Bavetta et al. (1999) "The effects of FK506 on dorsal column axons following spinal cord injury in adult rats: neuroprotection and local regeneration," Exp Neurol. 158:, 382-393.

Biomol Research Laboratories, Inc., Catalog Nos. PI100-0005 and PI100-0025, for ALLM (Calpain Inhibitor), available at www.biomol.com (last visited Dec. 7, 2007, 3 pages).

Bochelen et al. (1999) "Calcineurin inhibitors FK506 and SDZ ASM 981 alleviate the outcome of focal cerebral ischemic/reperfusion injury," J Pharmacol Exp Ther. 288: 653-659.

Butcher et al. (1997) "Neuroprotective actions of FK506 in experimental stroke: in vivo evidence against an antiexcitotoxic mechanism," J Neurosci. 17: 6939-6946.

Calbiochem Product No. MDL-28170, for Calpain Inhibitor III, available at www.emdbioscience.com (last visited Dec. 7, 2007, 2 pages).

Calbiochem Product No. SJA6017, for Calpain Inhibitor VI, available at, www.emdbioscience.com (last visited Dec. 7, 2007, 2 pages).

Campbell et al. (1999) "Spontaneous axonal regeneration after optic nerve injury in adult rat," Neuroreport 10(18): 3955-60.

Chatterjee et al. (1997) "Synthesis and Biological Activity of a Series of Potent Fluoromethyl Ketone Inhibitors of Recombinant Human Calpain I," J Med Chem. 40: 3820-3838.

Cheng et al. (1998) "Caspase Inhibitor Affords Neuroprotection with delayed administration in a rat model of neonatal hypoxic-ischemic brain injury," J Clin Invest. 101:, 1992-1999.

Dumont (2000) "FK506, an immunosuppressant targeting calcineurin function," Curr Med Chem. 7: 731-748.

Endres et al. (1998) J Cereb Blood Flow Metab. 18:, 238-247.

Esson (2004) "Microarray analysis of the failure of filtering blebs in a rat model of glaucoma filtering surgery," Invest Ophthalmol Vis Sci. 45(12):4450-62.

Freeman et al. (2000) "The effects of FK506 on retinal ganglion cells after optic nerve crush," Invest Ophthalmol Vis Sci. 41: 1111-15.

Garcia-Valenzuela et al. (1995) "Programmed cell death of retinal ganglion cells during experimental glaucoma," Exp Eye Res. 61:, 33-44.

Grosskreutz et al. (2005) "FK506 blocks activation of the intrinsic caspase cascade after optic nerve crush," Exp Eye Res. 80(5):681-86.

Grosskreutz et al. (2004), Calcineurin Activation in Experimental Glaucoma in the Rat, Invest Ophthalmol Vis Sci. 45: E-Abstract 2150-B961.

Guo et al. (2003) "Cyclophilin ligands protect against light-induced retinal degeneration in mice." Society for NeuroScience Abstract Viewer and Itinerary Planner: Abstract No. 816.8.

Hanninen et al. (2002) "Activation of caspase 9 in a rat model of experimental glaucoma," Curr Eye Res. 25:, 389-395.

Harriman et al. (2000) "Efficacy of Novel Calpain inhibitors in preventing Renal Cell death," J Pharmacol Exper Therapeut. 294(3):1083-1087.

Harriman et al. (2002) "Endoplasmic reticulum Ca2+ signaling and calpains mediate renal cell death," Cell Death Different. 9:734-741.

Herr et al. (1999) "FK506 prevents stroke-induced generation of ceramide and apoptosis signaling," Brain Res. 826:, 210-219.

Huang et al. (2005) "Calcineurin Cleavage Is Triggered By Elevated Intraocular Pressure And Calcineurin Inhibition Blocks Retinal Ganglion Cell Death In Experimental Glaucoma" Proc Natl Acad Sci USA 102(34):12242-47.

Huang et al. (2005) "Neuroprotection From Calcineurin-Mediated Retinal Ganglion Cell Apoptosis by FK506 in Experimental Glaucoma," Invest. Ophthalmol. Vis. Sci. 46: E-Abstract 4726.

Huang et al. (2006) "Calcineurin cleavage is mediated by calpain in experimental glaucoma: a proteomic analysis," Invest Ophthalmol Vis Sci. 47: E-Abstract 196.

Huang et al. (2005) "Transcriptional up-regulation and activation of initiating caspases in experimental glaucoma," Amer J Pathol. 167(3): 673-81.

International Search Report for international application PCT/US2006/030688, mailed on Mar. 13, 2007 (8 pages).

Jayanthi et al. (2005) "Calcineurin/NFAT-induced up-regulation of the FAS ligand / FAS death pathway is involved in methamphetamine-induced neuronal apoptosis," Proc. Natl. Acad. Sci. USA 102: 868-873.

Kaminska et al. (2004) "Molecular Mechanisms of Neuroprotective Action of Immunosuppressants facts and Hypotheses," J Cell Mol Med. 8(1) 45-58.

Kerrigan et al. (1997) Arch. Ophthalmol. 115:, 1031-1035.

Kikuchi et al. (1998) "Protective effects of FK506 against glutamate-induced neurotoxicity in retinal cell culture," Invest Ophthalmol Vis Sci. 39(7):1227-32.

Klettner et al. (2003) "The immunophilin-ligands FK506 and V-10,367 mediate neuroprotection by the heat shock shock response," Br J Pharmacol. 138: 1004-1012.

Klettner et al. (2003) "FK506 and its analogs—therapeutic potential for neurological disorders," Curr. Drug Targets CNS Neurol. Disord. 2: 153-162.

Lang-Lazdunski et al. (2001) "The effects of FK506 on neurologic and histopathologic outcome after transient spinal cord ischemia induced by aortic cross-clamping in rats," Anesth Analg. 92: 1237-1244.

Leamey et al. (2003) Role of calcineurin in activity-dependent pattern formation in the dorsal lateral geniculate nucleus of the ferret. Sur M.J Neurobiol. 56(2):153-62.

Levi et al. (2004) "A review of neuroprotective agents," Curr Med Chem. 11(18): 2383-97.

Li et al. (1993) "Peptide alpha-Keto Ester, alpha-Keto Amide, and alpha-Keto Acid Inhibitors of Calpains and Other Cysteine Proteases," J. Med. Chem. 36(22): 3472-80.

Li et al. (1996) "Novel Peptidyl alpha-Keto Amide Inhibitors of Calpains and Other Cysteine Proteases," J. Med. Chem. 39(20) 4089-98.

Liu et al. (2001) "Calpains mediate acute renal cell death: role of autolysis and translocation," Am. J. Physiol. Renal Physiol. 281:728-738.

Liu et al. (2002) "Cryoprotective Properties of Novel Nonpeptide Calpain Inhibitors in Renal Cells," J Pharmacol Exper Therapeut. 302(1): 88-94.

Liu et al. (2004) "The role of Calpain in Oncotic Cell Death," 44: 349-70.

Maeda et al. (2004) "A novel neuroprotectant against retinal ganglion cell damage in a glaucoma model and an optic nerve crush model in the rat," Invest Ophthalmol Vis Sci. 45: 851-56.

McKinnon et al. (2002) "Caspase activation and amyloid precursor protein cleavage in rat ocular hypertension," Invest Ophthalmol Visual Sci. 43: 1077-1087.

McKinnon et al. (2002) "Baculoviral IAP repeat-containing-4 protects optic nerve axons in a rat glaucoma model," Mol. Ther. 5: 780-787.

Mehendale et al. (2005) "Calpain: a death protein that mediates progression of liver injury," Trends in Pharmacol Sci. 26(5): 232-36.

Merops—The Peptidase Database, for leupeptin, available at www.merops.sanger.ac.uk (last visited Dec. 7, 2007, 1 page).

Mitchell et al. (1996) Ophthalmology 103:1661-1669.

Miyazawa et al. (2000) "Protective effect of FK506 in the reperfusion model after short-term occlusion of the middle cerebral artery in the rat: assessment by autoradiography using [125I]PK-11195," Neurol. Res. 22:, 630-633.

Molkentin et al. (1998) A calcineurin-dependent transcriptional pathway for cardiac hypertrophy. Cell 93(2): p. 215-28.

Mukerjee et al. (2000) Caspase-mediated proteolytic activation of calcineurin in thapsigargin-mediated apoptosis in SH-SY5Y neuroblastoma cells. Arch Biochem Biophys, 2000. 379(2): p. 337-43.

Nakazawa et al. (2001) "Localization of calcineurin in the mature and developing retina," J Histochem Cytochem. 49(2): 187-195.

Oka et al. (2005) "Involvement of Calpain in Retinal Degeneration Induced by N-Methyl-N-Nitrosourea in the Rats," Invest. Ophthalmol. Vis. Sci. 2005 46: E-Abstract 5255.

Pachydaki et al. (2006) "Effect of Systemic Administration of FK506 in a Rat Model of Retinal Detachment," Invest. Ophthalmol. Vis. Sci. 47: E-Abstract 1045.

Park et al. (2000) "A second calcineurin binding site on the NFAT regulatory domain," Proc Natl Acad Sci USA 97: 7130-7135.

Perche et al. (2005) Light-induced retinal apoptosis is caspase-dependent, Invest Ophthalmol Vis Sci. 46: E-Abstract 1666.

Quigley et al. (1995) "Retinal ganglion cell death in experimental glaucoma and after axotony occurs by apoptosis," Invest. Ophthalmol. Visual Sci. 36(5): 774-786.

Rao et al. (1997) "Transcription factors of the NFAT family," Ann Rev Immunot 15: 707-47.

Rokosz et al. (1995) "Reconstitution of active human calcineurin from recombinant subunits expressed in bacteria," Protein Exp. Purif. 6: 655-664.

Rosenstiel et al. (2003) "Differential effects of immunophilin-ligands (FK506 and V-10,367) on survival and regeneration of rat retinal ganglion cells in vitro and after optic nerve crush in vivo," J Neurotrauma. 20(3):297-307.

Sakurai et al. (2003) "Scleral plug of biodegradable polymers containing tacrolimus (FK506) for experimental uveitis," Invest Ophthalmol Vis Sci. 44(11): 4845-52.

Seitz et al. (2002) "Localization and characterization of calcineurin in bovine eye," Invest. Ophthalmol. Visual Sci. 43: 15-21.

Sharkey et al. (1994) "Immunophilins mediate the neuroprotective effects of FK506 in focal cerebral ischaemia," Nature 371: 336-339.

Shibasaki et al. (1996) Role of kinases and the phospahateose calcineurin inthe nuclear shuttling of transcription factor NF-AT4. Nature 382: 370-373.

Shindo et al. (2003) "Intravitreal injection of tacrolimus (FK506) suppresses experimental uveitis without damaging the retina in rabbit," Invest Ophthalmol Vis Sci. 44: E-Abstract 4595.

Sigma Aldrich, Catalog No. A6185, for Calpain Inhibitor I, available at www.sigmaaldrich.com (last visited Dec. 7, 2007, 3 pages).

Sommer et al. (1991) Arch. Ophthalmol. 109:, 1090-1095.

Springer et al. (2000) "Calcineurin-mediated BAD dephosphorylation activates the caspase-3 apoptotic cascade in traumatic spinal cord injury," J. Neurosci. 20: 7246-7251.

Steiner et al. (1992) "High brain densities of the immunophilin FKBP colocalized with calcineurin," Nature 358: 584-587.

Terada (2003) "Inhibition of excitatory neuronal cell death by cell-permeable calcineurin autoinhibitory peptide," J Neurochem. 87(5): 1145-51.

Tompa et al. (2004) "On Sequential Determinants of Calpain Cleavage," J. Biol. Chem. 279(20): 20775-85.

Tsujikawa et al. (1998) "Tacrolimus (FK506) attenuates leukocyte accumulation after transient retinal ischemia," Stroke 29(7): 1431-38.

U.S. National Library of medicine's ChemIDPluse® search results for quinolinecarboxamides showing four records: 2-Quinolinecarboxamide (RN: 5382-42-3), 8-Quinolinecarboxamide (RN: 55706-61-1), 2-Quinoxalinecarboxamide (RN: 5182-90-1), Quinoxaline-2-carboxamide (RN: 5182-90-1)(duplicate of previous record), available at www.chem.sis.nlm.nih.gov/chemidplus/chemidlite.jsp (last visited Dec. 7, 2007, 7 pages).

Wang et al. (1989) "Characterization of the fragmented forms of calcineurin produced by calpain I," Biochem Cell Biol. 67(10): 703-11.

Wang et al. (1996) "An alpha-mercaptoacrylic acid derivative is a selective nonpeptide cell-permeable calpain inhibitor and is neuroprotective," PNAS 93: 6687-6692.

Wang et al. (1999) "Ca2+-induced apoptosis through calcineurin dephosphorylation of BAD," Science 284(5412): 339-43.

Wang et al. (2000) "Calpain and caspase: can you tell the difference?" TINS 23(1): 20-26.

Wax et al. (1998) "Clinical and ocular histopathological findings in a patient with normal-pressure glaucoma," Arch. Ophthalmol. 116: 993-1001.

Winter et al. (2000) "The immunophilin ligand FK606, but not GPI-1046, protects against neuronal death and inhibits c-Jun expression in the substantia nigra pars compacta following transection of the rat medial forebrain bundle," Neuroscience 95: 753-762.

Wu et al. (2004) "Critical role of calpain-mediated cleavage of calcineurin in excitotoxic neurodegeneration," J Biol Chem 279(6): 4929-40.

Zacks, et al. (2003) "Caspase Activation in an Experimental Model of Retinal Detachment Invest," Ophthalmol. Vis. Sci. 44: 1262-1267.

Ahmed et al. (2004), Microarray analysis of changes in mRNA levels in the rat retina after experimental elevation of intraocular pressure. Invest Ophthalmol Vis Sci, 45: 1247-58.

Coleman et al. (2005) "Axon degeneration mechanisms: commonality amid diversity," Nat Rev Neurosci. 6: 889-98.

Guo et al. (2006) "Assessment of neuroprotective effects of glutamate modulation on glaucoma-related retinal ganglion cell apoptosis in vivo," Invest Ophthalmol Vis Sci. 47:626-33.

Ji et al. (2005) "Effects of elevated intraocular pressure on mouse retinal ganglion cells," Vision Res. 45:169-79.

Levkovitch-Verbin et al. (2006) "Minocycline Delays Death of Retinal Ganglion Cells in Experimental Glaucoma and After Optic Nerve Transection," Arch Ophthalmol. 124:520-26.

Nakazawa et al. (2005), Selective up-regulation of RB3/stathmin4 by ciliary neurotrophic factor following optic nerve axotomy, Brain Res, 1061(2):97-106.

Raivich et al. (2003), Lymphocyte infiltration in the injured brain: role of proinflammatory cytokines, J Neurosci Res, 72:726-33.

Stys et al. (2005), General mechanisms of axonal damage and its prevention, J Neural Sci, 233:3-13.

Lewis et al. (1999) "Effects of the Neurotrophin Brain-Derived Neurotrophic Factor in an Experimental Model of Retinal Detachment" Investigative Ophthalmology & Visual Science, vol. 40, No. 7, pp. 1530-1544.

Mehdi et al. (1990) "The inhibition of human neutrophil elastase and cathepsin G by peptidyl 1,2 dicarbonyl derivatives" Biochem Biophys Res Commun., 166(2): pp. 565-900 (Abstract only).

Peet et al. (1990) "Synthesis of peptidyl fluoromethyl ketones and peptidyl α-keto esters as inhibitors of porcine pancreatic elastase, human neutrophil elastase, and rat and human neutrophil cathepsin G" J. of Medicinal Chemistry, 33(1): pp. 394-407.

* cited by examiner

Duration of detachment (Days)

Duration of detachment (Days)

Duration of detachment (Days)

Duration of detachment (Days)

METHODS AND COMPOSITIONS FOR PRESERVING THE VIABILITY OF PHOTORECEPTOR CELLS

CROSS-REFERENCE TO RELATED APPLICATIONS

The present application claims the benefit of and priority to U.S. Provisional Patent Application Ser. No. 60/706,376, filed Aug. 8, 2005, and U.S. Provisional Patent Application Ser. No. 60/773,898, filed Feb. 16, 2006, the entire disclosures of which are incorporated by reference herein for all purposes.

FIELD OF THE INVENTION

The invention relates generally to methods and compositions for preserving the viability of photoreceptor cells following retinal detachment, and more particularly the invention relates to compositions including, for example, a neuroprotective agent, and their use in maintaining the viability of photoreceptor cells following retinal detachment.

BACKGROUND

The retina is a delicate neural tissue lining the back of the eye that converts light stimuli into electric signals for processing by the brain. Within the eye, the retina is disposed upon underlying retinal pigment epithelium and choroid, which provide the retina with a supply of blood and nutrients. A common and potentially blinding condition known as retinal detachment occurs when the retina becomes disassociated from its underlying retinal pigment epithelium and/or choroid with the accumulation of fluid in the intervening space. The loss of visual function appears to be more pronounced when the retinal detachments involve the central macula.

Unless treated, retinal detachments often result in irreversible visual dysfunction, which can range from partial to complete blindness. The visual dysfunction is believed to result from the death of photoreceptor cells, which can occur during the period when the retina is detached from its underlying blood and nutrient supply. Reattachment of the retina to the back surface of the eye typically is accomplished surgically, and despite the good anatomical results of these surgeries (i.e., reattachment of the retina) patients often are still left with permanent visual dysfunction.

There is still a need for new methods and compositions for maintaining the viability of photoreceptor cells following retinal detachment and for preserving vision when the retina ultimately becomes reattached.

SUMMARY OF THE INVENTION

Calcineurin activation and the presence of a truncated, constitutively active form of calcineurin is increased in the retina following retinal detachment. Modulating the activity of one or both of these targets provides a neuroprotective effect in the retina. Thus, modulating calcineurin can maintain the viability of photoreceptor cells following retinal detachment and preserve vision when the retina is reattached. Although the text herein focuses on preservation of the viability of photoreceptor cells, it should be understood that it is contemplated that compositions and methods according to the invention may be useful to preserve the viability of retinal ganglion cells, amacrine cells, retinal glia (including Müller glia), horizontal cells, bipolar cells, retinal vascular endothelial cells, retinal pericytes, astrocytes, retinal pigment epithelial cells, and choroidal vascular cells as well.

In one aspect, the invention provides a method of preserving the viability of photoreceptor cells disposed within a retina of a mammalian eye following retinal detachment. The method includes administering to a mammal having an eye in which a region of the retina has been detached an amount of a neuroprotective agent selected from a substance capable of suppressing endogenous calcineurin or constitutively active calcineurin, inhibiting cleavage of calcineurin to constitutively active calcineurin, and/or directly or indirectly antagonizing calcineurin or constitutively active calcineurin (and combinations thereof) sufficient to preserve the viability of photoreceptor cells disposed within the region of the detached retina. Suppressing endogenous calcineurin or constitutively active calcineurin includes, but is not limited to, suppressing or otherwise interfering with expression of the gene encoding the phosphatase, suppressing or otherwise interfering with the transcription of the gene into mRNA, and/or suppressing or otherwise interfering with the translation of the mRNA from the phosphatase gene into a functional protein.

This aspect can have any of the following features. The neuroprotective agent can be administered to the mammal prior to reattachment of the region of detached retina. The neuroprotective agent can be administered to the mammal during reattachment of the region of detached retina. The neuroprotective agent can be administered to the mammal after reattachment of the region of detached retina. The neuroprotective agent can be administered locally or systemically. A plurality of neuroprotective agents can be administered to the mammal. At least one neuroprotective agent can be administered by intraocular, intravitreal, or transcleral administration. The neuroprotective agent can reduce the number of photoreceptor cells in the region that die following retinal detachment. The retinal detachment can occur as a result of a retinal tear, retinoblastoma, melanoma, diabetic retinopathy, uveitis, choroidal neovascularization, retinal ischemia, pathologic myopia, hemorrhage, or trauma. The neuroprotective agent can be FK506, cyclosporin, asomycin, Ac-Leu-Leu-Met-H (aldehyde) ("ALLM"), peptide aldehydes (e.g., leupeptin), calpeptin (Z-Leu-Nle-H), alpha-dicarbonyls, nonpeptide quinolinecarboxamides, nonpeptide alpha-mercaptoacrylic acids and phosphorus derivatives, epoxysuccinates (e.g., E64), acyloxymethyl ketones, halomethylketones, solfonium methyl ketones, diazomethyl ketones, Z-Leu-Abu-CONHEt (AK275), 27-mer calpastatin peptide, Calpain Inhibitor I, Calpain Inhibitor II, Calpain Inhibitor III, Calpain Inhibitor IV, Calpain Inhibitor V, Calpain Inhibitor VI, Calpain Inhibitor VII, Cbz-Val-Phe-H (MDL28170), 3-(4-iodophenyl)-2-mercapto-(Z)-2-propenoic acid (PD150606), chloroacetic acid N'-(6,7-dichloro-4-phenyl-3-oxo-3,4-dihydroquino-xalin-2-yl)hydrazide (SJA-7029), peptidyl alpha-keto amides, CEP-4143, Cbz-Leu-Leu-Tyr-CHN$_2$, and combinations thereof. Neuroprotective agents include cyclophilin-binding calcineurin inhibitors, such as cyclosporins or cyclosporin derivatives, and macrophilin-binding calcineurin inhibitors, such as asomycin and asomycin derivatives.

In another aspect, the invention provides a method of preserving the viability of photoreceptor cells in a mammalian eye following retinal detachment. More particularly, the invention provides a method of preserving the viability of photoreceptor cells disposed within a region of a retina that has become detached from its underlying retinal pigment epithelium and/or choroid. The method comprises administering to a mammal in need of such treatment an amount of a neuroprotective agent sufficient to preserve the viability of photoreceptor cells, for example, rods and/or cones, disposed within the region of the detached retina. Administration of the neuroprotective agent minimizes the loss of visual function resulting from the retinal detachment.

The neuroprotective agent reduces the number of photoreceptor cells in the region of the retina that, without treatment, would die following retinal detachment. It is understood that photoreceptor cells in the retina may die via a variety of cell death pathways, for example, via apoptotic and necrotic cell death pathways. It has been found, however, that upon retinal detachment, the photoreceptor cells undergo apoptotic cell death in the detached portion of the retina. Furthermore, one or more caspases, for example, caspase 3, caspase 7 and caspase 9, participate in the cascade of events leading to apoptotic cell death. Accordingly, neuroprotective agents useful in the practice of the invention can include, for example, an apoptosis inhibitor, for example, a caspase inhibitor, for example, one or more of, a caspase 3 inhibitor, a caspase 7 inhibitor, and a caspase 9 inhibitor.

Because photoreceptors die as a result of retinal detachment, administration of neuroprotective agents minimize or reduce the loss of photoreceptor cell viability until such time the retina becomes reattached to the choroid and an adequate blood and nutrient supply is once again restored. The neuroprotective agent minimizes the level of photoreceptor cell death, and maintains photoreceptor cell viability prior to reattachment of the detached region of the retina. Under certain circumstances, however, it may be beneficial to administer the neuroprotective agent for a period of time after a retinal detachment has been detected and/or the retina surgically reattached. This period of time may vary and can include, for example, a period of a week, two weeks, three weeks, a month, three months, six months, nine months, a year, and two years, after surgical reattachment.

The neuroprotective agent, for example, can be administered, either alone or in combination with a pharmaceutically acceptable carrier or excipient, by one or more routes. For example, the neuroprotective agent may be administered systemically, for example, via oral or parenteral routes, for example, via intravascular, intramuscular or subcutaneous routes. Alternatively, the neuroprotective agent may be administered locally, for example, via intraocular, intravitreal, intraorbital, or transcleral routes. Furthermore, it is contemplated that a plurality of neuroprotective agents, for example, a substance capable of suppressing endogenous calcineurin or constitutively active calcineurin, inhibiting cleavage of calcineurin to constitutively active calcineurin, and/or directly or indirectly antagonizing calcineurin or constitutively active calcineurin (and combinations thereof), one or more caspase inhibitors, and combinations thereof, may be administered to the mammal to maintain viability of the photoreceptor cells disposed within the detached portion of the retina.

It is contemplated that the practice of the invention will be helpful in maintaining the viability of photoreceptor cells in retinal detachments irrespective of how the retinal detachments were caused. For example, it is contemplated that the practice of the method of the invention will be helpful in minimizing visual dysfunction resulting from retinal detachments caused by one or more of the following: a retinal tear, retinoblastoma, melanoma, diabetic retinopathy, uveitis, choroidal neovascularization, retinal ischemia, pathologic myopia, and trauma.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described below in which.

DETAILED DESCRIPTION

Figure 1:
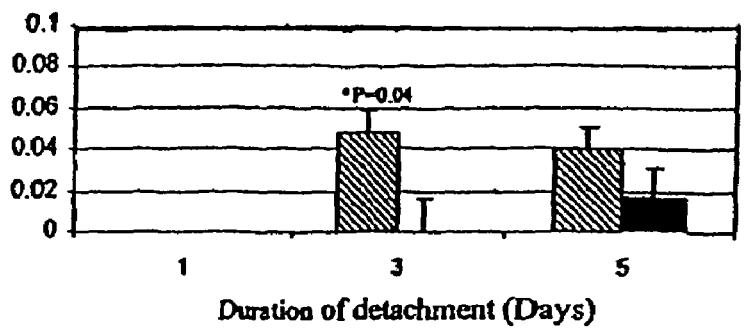
FIG. 1 depicts a bar chart showing the ratio of cleaved caspase 3 to pro-caspase 3 in densitometry units in detached retinas (hatched bars) and attached retinas (solid bars) at one, three and five days post retinal detachment.

During retinal detachment, the entire retina or a portion of the retina becomes dissociated from the underlying retinal pigment epithelium and choroid. As a result, the sensitive photoreceptor cells disposed in the detached portion of the retina become deprived of their normal supply of blood and nutrients. If untreated, the retina or more particularly the sensitive photoreceptor cells disposed within the retina die causing partial or even complete blindness. Accordingly, there is an ongoing need for methods and compositions that preserve the viability of photoreceptor cells following retinal detachment. If photoreceptor cell death can be minimized during retinal detachment, the affected photoreceptors likely will survive once the retina is reattached to the underlying retinal pigment epithelium and choroid, and the photoreceptors regain their normal blood and nutrient supply.

Retinal detachment can occur for a variety of reasons. The most common reason for retinal detachment involves retinal tears. Retinal detachments, however, can also occur because of, for example, retinoblastomas and other ocular tumors (for example, angiomas, melanomas, and lymphomas), diabetic retinopathy, retinal vascular diseases, uveitis, retinal ischemia and trauma. Furthermore, retinal detachments can occur as a result of formation of choroidal neovascularizations secondary to, for example, the neovascular form of age-related macular degeneration, pathologic myopia, and ocular histoplasmosis syndrome. It is understood that the clinical pathologies of retinal detachments are different from those of degenerative retinal disorders, for example, retinitis pigmentosa and age-related macular degeneration. However, the neuroprotective agents discussed herein may be useful in treating retinal detachments that occur secondary to an underlying degenerative retinal disorder. Accordingly, it is contemplated that the methods and compositions of the invention may be useful in minimizing or otherwise reducing photoreceptor cell death following retinal detachment, irrespective of the cause of the detachment.

The invention provides a method of preserving the viability of photoreceptor cells in a mammalian, for example, a primate, for example, a human, eye following retinal detachment. More particularly, the invention provides a method of preserving the viability of photoreceptor cells disposed within a region of a retina, which has become detached from its underlying retinal pigment epithelium and/or choroid. The method may be particularly helpful in preventing vision loss when the region of detachment includes at least a portion of the macula. The method comprises administering to a mammal in need of such treatment an amount of a neuroprotective agent sufficient to preserve the viability of photoreceptor cells disposed within the region of the detached retina.

As used herein, the term "neuroprotective agent" means any agent that, when administered to a mammal, either alone or in combination with other agents, minimizes or eliminates photoreceptor cell death (including both necrotic and apoptotic cell death) in a region of the retina that has become detached from the underlying retinal pigment epithelium and/or choroid. Although the text herein focuses on preservation of the viability of photoreceptor cells, it should be understood that it is contemplated that compositions and methods according to the invention may be useful to preserve the viability of retinal ganglion cells, amacrine cells, retinal glia (including Müller glia), horizontal cells, bipolar cells, retinal vascular endothelial cells, retinal pericytes, astrocytes, retinal pigment epithelial cells, and choroidal vascular cells as well. It is contemplated that useful neuroprotective agents include, for example, a substance capable of suppressing endogenous calcineurin or constitutively active calcineurin, inhibiting cleavage of calcineurin to constitutively active calcineurin, and/or directly or indirectly antagonizing calcineurin or constitutively active calcineurin (and combinations thereof), apoptosis inhibitors, for example, caspase inhibitors, and certain neurotrophic factors that prevent the onset or progression of apoptosis. More specifically, useful neuroprotective agents may include, for example, a protein (for example, a growth factor, antibody or an antigen binding fragment thereof), a peptide (for example, an amino acid sequence less than about 25 amino acids in length, and optionally an amino acid sequence less that about 15 amino acids in length), a nucleic acid (for example, a deoxyribonucleic acid, ribonucleic acid, an antisense oligonucleotide, or an aptamer), a peptidyl nucleic acid (for example, an antisense peptidyl nucleic acid), an organic molecule or an inorganic molecule, which upon administration minimizes photoreceptor cell death following retinal detachment. Additionally, interfering RNA (RNAi) techniques can be used. Neuroprotective agents alternatively or additionally may protect against gliosis.

It is understood that photoreceptor cell death during retinal detachments may occur as a result of either necrotic or apoptotic (also known as programmed cell death) pathways. Both of these pathways are discussed in detail in, for example, Kerr et al (1972) BR. J. CANCER 26: 239-257, Wyllie et al. (1980) INT. REV. CYTOLOGY 68: 251-306; Walker et al. (1988) METH. ACHIE. EXP. PATHOL. 13: 18-54 and Oppenheim (1991) ANN. REV. NEUROSCI. 14: 453-501. Apoptosis involves the orderly breakdown and packaging of cellular components and their subsequent removal by surrounding structures (Afford & Randhawa (2000) J. CLIN. PATHOL. 53:55-63). In general, apoptosis, also referred to as an apoptotic pathway, does not result in the activation of an inflammatory response. This is in contrast to necrotic cell death, which is characterized by the random breakdown of cells in the setting of an inflammatory response. Typically, during necrosis, also known as a necrotic pathway, a catastrophic event, for example, trauma, inflammation, ischemia or infection, typically causes uncontrolled death of a large group of cells. There are a variety of assays available for determining whether cell death is occurring via a necrotic pathway or an apoptotic pathway (see, for example, Cook et al. (1995) INVEST. OPHTHALMOL. VIS. SCI. 36:990-996).

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) BR. J. CANCER 26: 239-257). Assays for detecting the presence of apoptotic pathways include measuring morphologic and biochemical stigmata associated with cellular breakdown and packaging, such as pyknotic nuclei, apoptotic bodies (vesicles containing degraded cell components) and internucleosomally cleaved DNA. This last feature is specifically detected by binding and labeling the exposed 3'-OH groups of the cleaved DNA with the enzyme terminal deoxynucleotidyl transferase in the staining procedure often referred to as the TdT-dUTP Terminal Nick End-Labeling (TUNEL) staining procedure. It is believed that, at the core of this process lies a conserved set of serine proteases, called caspases, which are activated specifically in apoptotic cells.

There are approximately fourteen known caspases, and the activation of these proteins results in the proteolytic digestion of the cell and its contents. Each of the members of the caspase family possess an active-site cysteine and cleave substrates at Asp-Xxx bonds (i.e., after the aspartic acid residue). In general, a caspase's substrate specificity typically is determined by the four residues amino-terminal to the cleavage site. Caspases have been subdivided into subfamilies based on their substrate specificity, extent of sequence identity and structural similarities, and include, for example, caspase 1, caspase 2, caspase 3, caspase 4, caspase 5, caspase 6, caspase 7, caspase 8, caspase 9, caspase 10, caspase 11, caspase 12, caspase 13 and caspase 14. Monitoring their activity can be used to assess the level of on-going apoptosis.

Furthermore, it has been suggested that apoptosis is associated with the generation of reactive oxygen species, and that the product of the Bcl-$_2$ gene protects cells against apoptosis by inhibiting the generation or the action of the reactive oxygen species (Hockenbery et al. (1993) CELL 75: 241-251, Kane et al. (1993) SCIENCE 262: 1274-1277, Veis et al. (1993) CELL 75: 229-240, Virgili et al. (1998) FREE RADICALS BIOL. MED. 24: 93-101). Bcl-$_2$ belongs to a growing family of apoptosis regulatory gene products, which may either be death antagonists (Bcl-$_2$, Bcl-x$_L$) or death agonists (Bax, Bak) (Kroemer et al. (1997) NAT. MED. 3: 614-620). Control of cell death appears to be regulated by these interactions and by constitutive activities of the various family members (Hockenbery et al. (1993) CELL 75: 241-251). Several apoptotic pathways may coexist in mammalian cells that are preferentially activated in a stimulus-, stage-, context-specific and cell-type manner (Hakem et al. (1998) CELL 94: 339-352). However, it is contemplated that agents that upregulate the level of the Bcl-$_2$ gene expression or slow down the rate of breakdown of the Bcl-$_2$ gene product may be useful in the practice of the invention.

Useful apoptosis inhibitors include, for example, (i) proteins, for example, growth factors, cytokines, antibodies and antigen binding fragments thereof (for example, Fab, Fab', and Fv fragments), genetically engineered biosynthetic antibody binding sites, also known in the art as BABS or sFv's, and (ii) peptides, for example, synthetic peptides and derivatives thereof, which may be administered systemically or locally to the mammal. Other useful apoptosis inhibitors include, for example, deoxyribonucleic acids (for example, antisense oligonucleotides), ribonucleic acids (for example, antisense oligonucleotides and aptamers) and peptidyl nucleic acids, which once administered reduce or eliminate expression of certain genes, for example, caspase genes as in the case of anti-sense molecules, or can bind to and reduce or eliminate the activity of a target protein or receptor as in the case of aptamers. Additionally, RNAi techniques can be used. Other useful apoptosis inhibitors include small organic or inorganic molecules that reduce or eliminate apoptotic activity when administered to the mammal.

One set of apoptosis inhibitors useful in the practice of the invention include caspase inhibitors. Caspase inhibitors include molecules that inhibit or otherwise reduce the catalytic activity of a target caspase molecule (for example, a classical competitive or non-competitive inhibitor of catalytic activity) as well as molecules that prevent the onset or initiation of a caspase mediated apoptotic pathway.

With regard to the inhibitors of catalytic function, it is contemplated that useful caspase inhibitors include, on the one hand, broad spectrum inhibitors that reduce or eliminate the activity of a plurality of caspases or, on the other hand, specific caspase inhibitors that reduce or eliminate the activity of a single caspase. In general, caspase inhibitors act by binding the active site of a particular caspase enzyme and forming either a reversible or an irreversible linkage to target caspase molecule. Caspase inhibitors may include inhibitors of one or more of caspase 1, caspase 2, caspase 3, caspase 4, caspase 6, caspase 7, caspase 8, caspase 9, caspase 10, caspase 11, caspase 12, caspase 13, and caspase 14.

Useful caspase inhibitors include commercially available synthetic caspase inhibitors. Synthetic caspase inhibitors typically include a peptide recognition sequence attached to a functional group such as an aldehyde, chloromethylketone, fluoromethylketone, or fluoroacyloxymethylketone. Typically, synthetic caspase inhibitors with an aldehyde functional group reversibly bind to their target caspases, whereas the caspase inhibitors with the other functional groups tend to bind irreversibly to their targets. Useful caspase inhibitors, when modeled with Michaelis-Menten kinetics, preferably have a dissociation constant of the enzyme-inhibitor complex ($K_i$) lower than 100 μM, preferably lower than 50 μM, more preferably lower than 1 μM. The peptide recognition sequence corresponding to that found in endogenous substrates determines the specificity of a particular caspase. For example, peptides with the Ac-Tyr-Val-Ala-Asp-aldehyde (SEQ ID NO: 7) sequence are potent inhibitors of caspases 1 and 4 ($K_i$=10 nM), and are weak inhibitors of caspases 3 and 7 ($K_i \geqq 50$ μM). Removal of the tyrosine residue, however, results in a potent but less specific inhibitor. For example, 2-Val-Ala-Asp-fluoromethylketone inhibits caspases 1 and 4 as well as caspases 3 and 7.

Exemplary synthetic caspase 1 inhibitors, include, for example, Ac-N-Me-Tyr-Val-Ala-Asp-aldehyde (SEQ ID NO: 8), Ac-Trp-Glu-His-Asp-aldehyde (SEQ ID NO: 9), Ac-Tyr-N-Me-Val-Ala-N-Me-Asp-aldehyde (SEQ ID NO: 10), Ac-Tyr-Val-Ala-Asp-Aldehyde (SEQ ID NO: 7), Ac-Tyr-Val-Ala-Asp-chloromethylketone (SEQ ID NO: 7), Ac-Tyr-Val-Ala-Asp-2,6-dimethylbenzoyloxymethylketone (SEQ ID NO: 7), Ac-Tyr-Val-Ala-Asp(OtBu)-aldehyde-dimethyl acetol (SEQ ID NO: 14), Ac-Tyr-Val-Lys-Asp-aldehyde (SEQ ID NO: 15), Ac-Tyr-Val-Lys(biotinyl)-Asp-2,6-dimethylbenzoyloxymethylketone (SEQ ID NO: 16), biotinyl-Tyr-Val-Ala-Asp-chloromethylketone (SEQ ID NO: 7), Boc-Asp(OBzl)-chloromethylketone, ethoxycarbonyl-Ala-Tyr-Val-Ala-Asp-aldehyde (pseudo acid) (SEQ ID NO: 18), Z-Asp-2,6-dichlorobenzoyloxymethylketone, Z-Asp(OlBu)-bromomethylketone, Z-Tyr-Val-Ala-Asp-chloromethylketone (SEQ ID NO: 7), Z-Tyr-Val-Ala-DL-Asp-fluoromethlyketone (SEQ ID NO: 20), Z-Val-Ala-DL-Asp-fluoromethylketone, and Z-Val-Ala-DL-Asp(OMe)-fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac-Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone (SEQ ID NO: 7), Ac-Tyr-Val-Ala-Asp-acyloxymethylketone (SEQ ID NO: 7), Z-Asp-CH2-DCB, Z-Tyr-Val-Ala-Asp-fluoromethylketone (SEQ ID NO: 7), all of which can be obtained from Calbiochem, Calif.

Exemplary synthetic caspase 2 inhibitors, include, for example, Ac-Val-Asp-Val-Ala-Asp-aldehyde (SEQ ID NO: 22), which can be obtained from Bachem Bioscience Inc., PA, and Z-Val-Asp-Val-Ala-Asp-fluoromethylketone (SEO ID NO: 22), which can be obtained from Calbiochem, Calif.

Exemplary synthetic caspase 3 precursor protease inhibitors include, for example, Ac-Glu-Ser-Met-Asp-aldehyde (pseudo acid) (SEQ ID NO: 23) and Ac-Ile-Glu-Thr-Asp-aldehyde (pseudo acid) (SEQ ID NO: 24) which can be obtained from Bachem Bioscience Inc., PA. Exemplary synthetic caspase 3 inhibitors include, for example, Ac-Asp-Glu-Val-Asp-aldehyde (SEQ ID NO: 25), Ac-Asp-Met-Gin-Asp-aldehyde (SEQ ID NO: 26), biotinyl-Asp-Glu-Val-Asp-aldehyde (SEQ ID NO: 27), Z-Asp-Glu-Val-Asp-chloromethylketone (SEQ ID NO: 27), Z-Asp(OMe)-Glu(OMe)-Val-DL-Asp(OMe)-fluoromethylketone (SEQ ID NO: 28), and Z-Val-Ala-DL-Asp(OMe)-fluoromethylketone which can be obtained from Bachem Bioscience Inc., PA. Other exemplary caspase 3 inhibitors include, for example, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), Z-Asp-Glu-Val-Asp-fluoromethylketone (SEQ ID NO: 25), biotin-X-Asp-Glu-Val-Asp-fluoromethylketone (SEQ ID NO: 25), Ac-Asp-Glu-Val-Asp-chloromethylketone (SEQ ID NO: 25), which can be obtained from Calbiochem, Calif.

Exemplary synthetic caspase 4 inhibitors include, for example, Ac-Leu-Glu-Val-Asp-aldehyde (SEQ ID NO: 30) and Z-Tyr-Val-Ala-DL-Asp-fluoromethylketone (SEQ ID NO: 20), which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, Calif.

Exemplary synthetic caspase 5 inhibitors include, for example, Z-Trp-His-Glu-Asp-fluoromethylketone (SEQ ID NO: 11), which can be obtained from Calbiochem, Calif., and Ac-Trp-Glu-His-Asp-aldehyde (SEQ ID NO: 9) and Z-Trp-Glu(O-Me)-His-Asp(O-Me) fluoromethylketone (SEQ ID NO: 12), which can be obtained from Sigma Aldrich, Germany.

Exemplary synthetic caspase 6 inhibitors include, for example, Ac-Val-Glu-Ile-Asp-aldehyde (SEQ ID NO: 13), Z-Val-Glu-Ile-Asp-fluoromethylketone (SEQ ID NO: 13), and Ac-Ala-Ala-Val-Ala-Leu-Leu-Pro-Ala-Val-Leu-Leu-Ala-Leu-Leu-Ala-Pro-Val-Glu-Ile-Asp-aldehyde (SEQ ID NO: 4), which can be obtained from Calbiochem, Calif.

Exemplary synthetic caspase 7 inhibitors include, for example, Z-Asp(OMe)-Gln-Met-Asp(OMe) (SEQ ID NO: 17) fluoromethylketone, Ac-Asp-Glu-Val-Asp-aldehyde (SEQ ID NO: 25), Biotin-Asp-Glu-Val-Asp-fluoromethylketone (SEQ ID NO: 25), Z-Asp-Glu-Val-Asp-fluoromethylketone (SEQ ID NO: 25), Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde (SEQ ID NO: 25), Ac-Ile-Glu-Pro-Asp-aldehyde (SEQ ID NO: 19), Ac-Ile-Glu-Thr-Asp-aldehyde (SEQ ID NO: 24), Ac-Trp-Glu-His-Asp-aldehyde (SEQ ID NO: 9) and Boc-Ala-Glu-Val-Asp-aldehyde (SEQ ID NO: 21) which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Asp-fluoromethylketone (SEQ ID NO: 24), which can be obtained from Calbiochem, Calif.

Exemplary synthetic caspase 9 inhibitors, include, for example, Ac-Asp-Glu-Val-Asp-aldehyde (SEQ ID NO: 25), Ac-Leu-Glu-His-Asp-aldehyde (SEQ ID NO: 29), and Ac-Leu-Glu-His-Asp-chloromethylketone (SEQ ID NO: 29) which can be obtained from Bachem Bioscience Inc., PA. Other exemplary caspase 9 inhibitors include, for example, Z-Leu-Glu-His-Asp-fluoromethylketone (SEQ ID NO: 29) and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO: 6), which can be obtained from Calbiochem, Calif.

Furthermore, it is contemplated that caspase specific antibodies (for example, monoclonal or polyclonal antibodies, or antigen binding fragments thereof), for example, an antibody that specifically binds to and reduces the activity of, or inactivates a particular caspase may be useful in the practice of the invention. For example, an anti-caspase 3 antibody, an anti-caspase 7 antibody, or an anti-caspase 9 antibody may be useful in the practice of the invention. Additionally, it is contemplated that an anti-caspase aptamer that specifically binds and reduces the activity of, or inactivates a particular caspase, for example, an anti-caspase 3 aptamer, an anti-caspase 7 aptamer, or an anti-caspase 9 aptamer may be useful in the practice of the invention.

Alternatively, endogenous caspase inhibitors can be used to reduce, or inhibit caspase activity. For example, one useful class of endogenous caspase inhibitor includes proteins known as inhibitors of apoptosis proteins (IAPs) (Deveraux et al. (1998) EMBO JOURNAL 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al. (2000) J. BIOL. CHEM. 275: 9102-9105), including bioactive fragments and analogs thereof. Survivin has been reported to inhibit caspase-3 and caspase-7 activity. It is also contemplated that molecules that act through IAPs will also be useful, for example, VEGF has anti-apoptotic activity by acting through survivin.

In addition, it is contemplated that useful neuroprotective agents may include one or more neurotrophic factors, which may serve as effective apoptosis inhibitors (Lewis et al. (1999) INVEST. OPHTHALMOL. VIS. SCI. 40: 1530-44; LaVail et al. (1998) INVEST. OPHTHALMOL. VIS. Sci. 39: 592-602). Exemplary neurotrophic factors include, for example, Brain Derived Growth Factor (Caffe et al. (2001) INVEST OPHTHALMOL. VIS. SCI. 42: 275-82) including bioactive fragments and analogs thereof; Fibroblast Growth Factor (Bryckaert et al. (1999) ONCOGENE 18: 7584-7593) including bioactive fragments and analogs thereof; PEDF including bioactive fragments and analogs thereof; and Insulin-like Growth Factors, for example, IGF-I and IGF-II (Rukenstein et al. (1991) J NEUROSCI. 11:2552-2563) including bioactive fragments and analogs thereof; and cytokine-associated neurotrophic factors.

Bioactive fragments refer to portions of an intact template protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

With reference to the foregoing proteins, the term "analogs" includes variant sequences that are at least 80% similar or 70% identical, more preferably at least 90% similar or 80% identical, and most preferably 95% similar or 90% identical to at least a portion of one of the exemplary proteins described herein, for example, Brain Derived Growth Factor. To determine whether a candidate protein has the requisite percentage similarity or identity to a reference polypeptide, the candidate amino acid sequence and the reference amino acid sequence are first aligned using the dynamic programming algorithm described in Smith and Waterman (1981) J. MOL. BIOL. 147: 195-197, in combination with the BLOSUM62 substitution matrix described in FIG. 2 of Henikoff and Henikoff (1992), PROC. NAT. ACAD. SCI. USA 89:10915-10919. An appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art. Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity.

Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

Furthermore, by way of example, cAMP elevating agents may also serve as effective apoptosis inhibitors. Exemplary cAMP elevating agents include, for example, 8-(4-chlorophenylthio)-adenosine-3':5'-cyclic-monophosphate (CPTcAMP) (Koike (1992) PROG. NEURO-PSYCHOPHARMACOL. BIOL. PSYCHIAT. 16: 95-106), forskolin, isobutyl methylxanthine, cholera toxin (Martin et al. (1992) J. NEUROBIOL. 23:1205-1220), and 8-bromo-cAMP, $N^6,O^{2'}$-dibutyryl-cAMP and $N^6,O^{2'}$dioctanoyl-cAMP (Rydel and Greene (1988) PROC. NAT. ACAD. SCI. USA 85: 1257-1261).

Furthermore, other exemplary apoptosis inhibitors can include, for example, glutamate inhibitors, for example, NMDA receptor inhibitors (Bamford et al. (2000) EXP. CELL RES. 256: 1-11) such as eliprodil (Kapin et al. (1999) INVEST. OPHTHALMOL. VIS. SCI 40,1177-82) and MK-801 (Solberg et al. INVEST. OPHTHALMOL. VIS. SCI (1997) 38,1380-1389) and n-acetylated-αλπηα-linked-acidic dipeptidase inhibitors, such as, 2-(phosphonomethyl) pentanedioic acid (2-PMPA) (Harada et al. NEUR. LETT. (2000) 292,134-36); steroids, for example, hydrocortisone and dexamethasone (see, U.S. Pat. No. 5,840,719; Wenzel et al. (2001) INVEST. OPHTHALMOL. VIS. SCI. 42: 1653-9); nitric oxide synthase inhibitors (Donovan et al. (2001) J. BIOL. CHEM. 276: 23000-8); serine protease inhibitors, for example, 3,4-dichloroisocoumarin and N-tosyl-lysine chloromethyl ketone (see, U.S. Pat. No. 6,180,402); cysteine protease inhibitors, for example, N-ethylmaleimide and iodoacetamide, or an interleukin-1β-converting enzyme inhibitor, for example, Z-Asp-2,6-dichlorobenzoyloxymethylketone (see, U.S. Pat. No. 6,180,402); and antisense nucleic acid or peptidyl nucleic acid sequences that lower of prevent the expression of one or more of the death agonists, for example, the products of the Bax, and Bak genes.

In addition, or in the alternative, it may be useful to inhibit expression or activity of members of the caspase cascade that are upstream or downstream of caspase 3, caspase 7 and caspase 9. For example, it may be useful to inhibit PARP, which is a component of the apoptosis cascade downstream of caspase 7. An exemplary PARP inhibitor includes 3-aminobenzamide (Weise et al. (2001) CELL DEATH DIFFER. 8:801-807). Other examples include inhibitors of the expression or activity of Apoptosis Activating Factor-1 (Apaf-1) and/or cytochrome C. Apaf-1 and cytochrome C bind the activated form of caspase 9 to produce a complex, which is known to propagate the apoptosis cascade. Thus, any protein (for example, antibody), nucleic acid (for example, aptamer), peptidyl nucleic acid (for example, antisense molecule) or other molecule that inhibits or interferes with the binding of caspase 9 to Apaf-1/cytochrome C can serve to inhibit apoptosis.

Under certain circumstances, it may be advantageous to also administer to the individual undergoing treatment with the neuroprotective agent an anti-permeability agent and/or an inflammatory agent so as to minimize photoreceptor cell death. An anti-permeability agent is a molecule that reduces the permeability of normal blood vessels. Examples of such molecules include molecules that prevent or reduce the expression of genes encoding, for example, Vascular Endothelial Growth Factor (VEGF) or an Intercellular Adhesion Molecule (ICAM) (for example, ICAM-1, ICAM-2 or ICAM-3). Exemplary molecules include antisense oligonucleotides and antisense peptidyl nucleic acids that hybridize in vivo to a nucleic acid encoding a VEGF gene, an ICAM gene, or a regulatory element associated therewith. Other suitable molecules bind to and/or reduce the activity of, for example, the VEGF and ICAM molecules (for example, anti-VEGF and anti-ICAM antibodies and antigen binding fragments thereof, and anti-VEGF or anti-ICAM aptamers). Other suitable molecules bind to and prevent ligand binding and/or activation of a cognate receptor, for example, the VEGF receptor or the ICAM receptor. Such molecules may be administered to the individual in an amount sufficient to reduce the permeability of blood vessels in the eye. An anti-inflammatory agent is a molecule that prevents or reduces an inflammatory response in the eye and in some instances can be considered a neuroprotective agent. Exemplary anti-inflammatory agents include steroids, for example, hydrocortisone, dexamethasone sodium phosphate, and methylprediso- lone. Such molecules may be administered to the individual in an amount sufficient to reduce or eliminate an inflammatory response in the eye.

It is contemplated that the foregoing and other neuroprotective agents now known or hereafter discovered may be assayed for efficacy in minimizing photoreceptor cell death following retinal detachment using a variety of model systems. Basic techniques for inducing retinal detachment in various animal models are known in the art (see, for example, Anderson et al. (1983) INVEST. OPHTHALMOL. VIS. SCI. 24: 906-926; Cook et al. (1995) INVEST. OPHTHALMOL. VIS. SCI. 36: 990-996; Marc et al. (1998) OPHTHALMOL. VIS. SCI. 39: 1694-1702; Mervin et al. (1999) AM. J. OPHTHALMOL. 128: 155-164; Lewis et al. (1999) AM. J. OPHTHALMOL. 128: 165-172). Once a suitable animal model has been created (see, Example 1 below) an established or putative neuroprotective agent can be administered to an eye at different dosages. The ability of the neuroprotective agent and dosage required to maintain cell viability may be assayed by one or more of (i) tissue histology, (ii) TUNEL staining, which quantifies the number of TUNEL-positive cells per section, (iii) electron microscopy, (iv) immunoelectron microscopy to detect the level of, for example, apoptosis inducing factor (AIF) in the samples, and (v) immunochemical analyses, for example, via Western blotting, to detect the level of certain caspases in a sample.

The TUNEL technique is particularly useful in observing the level of apoptosis in photoreceptor cells. By observing the number of TUNEL-positive cells in a sample, it is possible to determine whether a particular neuroprotective agent is effective at minimizing or reducing the level of apoptosis, or eliminating apoptosis in a sample. For example, the potency of the neuroprotective agent will have an inverse relationship to the number of TUNEL-positive cells per sample. By comparing the efficacy of a variety of potential neuroprotective agents using these methods, it is possible to identify neuroprotective factors most useful in the practice of the invention.

The neuroprotective agent may be administered to the mammal from the time the retinal detachment is detected to the time the retina is repaired, for example, via surgical reattachment. It is understood, however, that under certain circumstances, it may be advantageous to administer the neuroprotective agent to the mammal even after the retina has been surgically repaired. For example, even after the surgical reattachment of a detached retina in patients with rhegmatogenous retinal detachments, persistent subretinal fluid may exist under the fovea as detected by ocular coherence tomography long after the surgery has been performed (see, Hagimura et al. (2002) AM. J. OPHTHALMOL. 133:516-520). As a result, even after surgical repair the retina may still not be completely reattached to the underlying retinal pigment epithelium and choroid. Furthermore, when retinal detachments occur secondary to another disorder, for example, the neovascular form of age-related macular degeneration and ocular melanomas, it may be beneficial to administer the neuroprotective agent to the individual while the underlying disorder is being treated so as to minimize loss of photoreceptor cell viability. Accordingly, in such cases, it may be advantageous to administer the neuroprotective agent to the mammal for one week, two weeks, three weeks, one month, three months, six months, nine months, one year, two years or more (i) after retinal detachment has been identified, and/or (ii) after surgical reattachment of the retina has occurred, and/or (iii) after detection of an underlying degenerative disorder, so as to minimize photoreceptor cell death.

Once the appropriate neuroprotective agents have been identified, they may be administered to the mammal of interest in any one of a wide variety of ways. It is contemplated that a neuroprotective agent, for example, a caspase inhibitor, can be administered either alone or in combination with another neuroprotective agent, for example, a neurotrophic agent. It is contemplated that the efficacy of the treatment may be enhanced by administering two, three, four or more different neuroprotective agents either together or one after the other. Although the best means of administering a particular neuroprotective agent or combination of neuroprotective agents may be determined empirically, it is contemplated that neuroprotective agents may be administered locally or systemically.

Systemic modes of administration include both oral and parenteral routes. Parenteral routes include, for example, intravenous, intraarterial, intramuscular, intradermal, subcutaneous, intranasal and intraperitoneal routes. It is contemplated that the neuroprotective agents administered systemically may be modified or formulated to target the neuroprotective agent to the eye. Local modes of administration include, for example, intraocular, intraorbital, subconjuctival, intravitreal, subretinal or transcleral routes. It is noted, however, that local routes of administration are preferred over systemic routes because significantly smaller amounts of the neuroprotective agent can exert an effect when administered locally (for example, intravitreally) versus when administered systemically (for example, intravenously). Furthermore, the local modes of administration can reduce or eliminate the incidence of potentially toxic side effects that may occur when therapeutically effective amounts of neuroprotective agent (i.e., an amount of a neuroprotective agent sufficient to reduce, minimize or eliminate the death of photoreceptor cells following retinal detachment) are administered systemically.

Administration may be provided as a periodic bolus (for example, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). The neuroprotective agent may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS. SCI. 41:1186-1191). A variety of devices suitable for administering a neuroprotective agent locally to the inside of the eye are known in the art. See, for example, U.S. Pat. Nos. 6,251,090, 6,299,895, 6,416,777, 6,413,540, and 6,375,972, and PCT/US00/28187.

The neuroprotective agent also may be administered in a pharmaceutically acceptable carrier or vehicle so that administration does not otherwise adversely affect the recipient's electrolyte and/or volume balance. The carrier may comprise, for example, physiologic saline or other buffer system.

In addition, it is contemplated that the neuroprotective agent may be formulated so as to permit release of the neuroprotective agent over a prolonged period of time. A release system can include a matrix of a biodegradable material or a material which releases the incorporated neuroprotective agent by diffusion. The neuroprotective agent can be homogeneously or heterogeneously distributed within the release system. A variety of release systems may be useful in the practice of the invention, however, the choice of the appropriate system will depend upon rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that neuroprotective agents having different molecular weights are released by diffusion through or degradation of the material.

Representative synthetic, biodegradable polymers include, for example: polyamides such as poly(amino acids) and poly (peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly (ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 μm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

The type and amount of neuroprotective agent administered may depend upon various factors including, for example, the age, weight, gender, and health of the individual to be treated, as well as the type and/or severity of the retinal detachment to be treated. As with the modes of administration, it is contemplated, that the optimal neuroprotective agents and dosages of those neuroprotective agents may be determined empirically. The neuroprotective agent preferably is administered in an amount and for a time sufficient to permit the survival of at least 25%, more preferably at least 50%, and most preferably at least 75%, of the photoreceptor cells in the detached region of the retina.

By way of example, small molecule, protein-, peptide- or nucleic acid-based neuroprotective agents can be administered at doses ranging, for example, from about 0.001 to about 500 mg/kg, optionally from about 0.01 to about 250 mg/kg, and optionally from about 0.1 to about 100 mg/kg. Nucleic acid-based neuroprotective agents may be administered at doses ranging from about 1 to about 20 mg/kg daily. Furthermore, antibodies that are neuroprotective agents may be administered intravenously at doses ranging from about 0.1 to about 5 mg/kg once every two to four weeks. With regard to intravitreal administration, the neuroprotective agents, for example, antibodies, may be administered periodically as boluses in dosages ranging from about 10 µg to about 5 mg/eye, and optionally from about 100 µg to about 2 mg/eye. With regard to transcleral administration, the neuroprotective agents may be administered periodically as boluses in dosages ranging from about 0.1 µg to about 1 mg/eye, and optionally from about 0.5 µg to about 0.5 mg/eye.

The present invention, therefore, includes the use of a neuroprotective agent, for example, a substance capable of suppressing endogenous calcineurin or constitutively active calcineurin, inhibiting cleavage of calcineurin to constitutively active calcineurin, and/or directly or indirectly antagonizing calcineurin or constitutively active calcineurin (and combinations thereof), in the preparation of a medicament for treating an ocular condition associated with a retinal detachment, for example, a loss of vision as a result of photoreceptor cell death in the region of retinal detachment. A composition comprising one or more neuroprotective agents, one agent optionally being a caspase inhibitor, may be provided for use in the present invention. The neuroprotective agent or agents may be provided in a kit which optionally may comprise a package insert with instructions for how to treat the patient with the retinal detachment. For each administration, the neuroprotective agent may be provided in unit-dosage or multiple-dosage form. Preferred dosages of the neuroprotective agents, however, are as described above.

Calcineurin is a $Ca^{++}$ calmodulin-dependent protein phosphatase that includes a 60 kDa calcineurin A subunit containing a catalytic domain (amino acids 20-340), a binding site for calmodulin, and a C terminal autoinhibitory domain. A constitutively active form of calcineurin can be formed by cleavage or truncation of the regulator domains, including the autoinhibitory domain. It has been shown that this truncated form leads to apoptosis of cultured neurons and that cell death is inhibited by FK506. In addition, calcineurin, in its native state is able to activate the apoptotic pathway when its active site is exposed.

More specifically, following activation by $Ca^{2+}$ influx, calcineurin dephosphorylates the proapoptotic $Bcl_{-2}$ family member, Bad, which translocates from the cytosol to the mitochondria where it complexes with other $Bcl_{-2}$ family members to cause the release of cyt c. Cyt c release facilitates aggregation of the apoptosome (cyt c, Apaf-1 and procaspase 9), leading to caspase 9 activation and initiation of the intrinsic caspase cascade. Calcineurin activation also plays a role in initiating the extrinsic, caspase 8, cascade. Activated calcineurin dephosphorylates nuclear factor of activated T-cells (NFAT), resulting in its nuclear translocation where it acts as a transcription factor for fasL, TNFalpha, and IL-2. Both fasL and TNFalpha are able to initiate activation of the caspase 8 pathway, thereby highlighting the central position of calcineurin in apoptotic cascades and calcineurin's potential to act in a coordinating role for cell death responses. Thus, activation of calcineurin may be expected to be pro-apoptotic by both pBad dephosphorylation and fasL upregulation.

A truncated, unregulated, and constitutively active form of calcineurin can be produced either by the action of the $Ca^{2+}$-dependent protease, calpain, or by caspase 3. This truncated form, which lacks the autoinhibitory domain but contains the active site, has been used effectively as a tool in designing studies to understand calcineurin's role in various cellular processes. Recently, however, this cleaved form of calcineurin has been reported to be associated with apoptosis and cell death in neurons in vitro and in vivo after kainate injection. In glaucoma animal models, a cleaved 45 kDa form of calcineurin has been observed that, by epitope mapping, has lost the C-terminal autoinhibitory domain. This form is seen in eyes with elevated intraocular pressure (IOP) but not in control eyes. (see Huang et al. (2005) PNAS U.S.A. 102 (34):12242-7, the entirety of which is incorporated herein by reference for all purposes). This same finding has been observed in a retinal detachment model (Example 3, below). Despite this cleavage, the phosphatase activity of cleaved calcineurin is inhibited by FK506, and retinal ganglion cell (RGC) death is blunted by FK506 in experimental glaucoma (see Huang et al. (2005) PNAS U.S.A. 102(34):12242-7). Similar blunting of photoreceptor death can be seen after retinal detachment in animals treated with FK506 (Examples 4 and 5, below).

As more fully described in Examples 3 and 4 below, calcineurin activation and/or removal of the autoinhibitory portion of calcineurin to produce a constitutively active form of calcineurin increase in retinas in response to detachment of the retina from the underlying choroidal tissue. Accordingly, to the extent the viability of photoreceptor cells disposed within a retina (as well as other cells disposed within the retina) is to be preserved, steps may be taken to exploit these natural biological responses by suppressing endogenous calcineurin or constitutively active calcineurin, inhibiting cleavage of calcineurin to constitutively active calcineurin (for example, by inhibiting calpain, such as with Ac-Leu-Leu-Met-H (aldehyde) ("ALLM")), and/or directly or indirectly antagonizing calcineurin or constitutively active calcineurin (and combinations thereof).

Insofar as activated calcineurin and cleaved calcineurin have pro-cell death activity, one may decrease the level of one or both of these molecules or otherwise antagonize one or both of their activities, in order to reduce the pro-cell death activity. Examples of the neuroprotective agents that can suppress endogenous calcineurin or constitutively active calcineurin, inhibit cleavage of calcineurin to constitutively active calcineurin, and/or directly or indirectly antagonize calcineurin or constitutively active calcineurin (and combinations thereof), include, for example, FK506, cyclosporin, asomycin, ALLM, peptide aldehydes (e.g., leupeptin), calpeptin (Z-Leu-Nle-H), alpha-dicarbonyls, nonpeptide quinolinecarboxamides, nonpeptide alpha-mercaptoacrylic acids and phosphorus derivatives, epoxysuccinates (e.g., E64), acyloxymethyl ketones, halomethylketones, solfonium methyl ketones, diazomethyl ketones, Z-Leu-Abu-CONHEt (AK275), 27-mer calpastatin peptide, Calpain Inhibitor I, Calpain Inhibitor II, Calpain Inhibitor III, Calpain Inhibitor IV, Calpain Inhibitor V, Calpain Inhibitor VI, Calpain Inhibitor VII, Cbz-Val-Phe-H (MDL28170), 3-(4-iodophenyl)-2-mercapto-(Z)-2-propenoic acid (PD150606), chloroacetic acid N'-(6,7-dichloro-4-phenyl-3-oxo-3,4-dihydroquino-xalin-2-yl)hydrazide (SJA-7029), peptidyl alpha-keto amides, CEP-4143, and Cbz-Leu-Leu-Tyr-$CHN_2$. Neuroprotective agents can also include growth factors, cytokines, antibodies and antigen binding fragments thereof (for example, Fab, Fab', and Fv fragments), genetically engineered biosynthetic antibody binding sites, also known in the art as BABS or sFv's, and peptides, for example, synthetic peptides and derivatives thereof, which may be administered to systemically or locally to the mammal. Other useful neuroprotective agents include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate expression of certain genes or can bind to and reduce or eliminate the activity of a target protein or receptor as in the case of aptamers. Other useful neuroprotective agents include small organic or inorganic molecules that reduce or eliminate activity when administered to the mammal. Any of these routes may preserve the viability of photoreceptor cells disposed within a retina. It should be understood that any of the dosage strategies, drug formulations, or administration schedules described above are applicable to all of these neuroprotective agents.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

EXAMPLES

Example 1

Detection of Caspase Activity Following Retinal Detachment

This example demonstrates that certain caspases, particularly caspases 3, 7 and 9, are activated in photoreceptor cells following retinal detachment.

Experimental retinal detachments were created using modifications of previously published protocols (Cook et al. (1995) INVEST. OPHTHALMOL. VIS. SCI. 36(6):990-6; Hisatomi et al. (2001) AM. J. PATH. 158(4):1271-8). Briefly, rats were anesthetized using a 50:50 mixture of ketamine (100 mg/ml) and xylazine (20 mg/ml). Pupils were dilated using a topically applied mixture of phenylephrine (5.0%) and tropicamide (0.8%). A 20 gauge micro-vitreoretinal blade was used to create a sclerotomy approximately 2 mm posterior to the limbus. Care was taken not to damage the lens during the sclerotomy procedure. A Glaser subretinal injector (20 gauge shaft with a 32 gauge tip, Becton-Dickinson, Franklin Lakes, N.J.) connected to a syringe filled with 10 mg/ml of Healon® sodium hyaluronate (Pharmacia and Upjohn Company, Kalamazoo, Mich.) then was introduced into the vitreous cavity. The tip of the subretinal injector was used to create a retinotomy in the peripheral retina, and then the sodium hyaluronate was slowly injected into the subretinal space to elevate the retina from the underlying retinal pigment epithelium. Retinal detachments were created only in the left eye (OS) of each animal, with the right eye (OD) serving as the control. In each experimental eye, approximately one half of the retina was detached, allowing the attached portion to serve as a further control.

Following creation of the experimental retinal detachment, intraocular pressures were measured before and immediately after retinal detachment with a Tono-pen. No differences in intraocular pressures were noted. The retinal break created by the subretinal injector was confined only to the site of the injection.

Light microscopic analysis of the detached retinas showed an increase in morphologic stigmata of apoptosis as a function of time after detachment. Eyes then were enucleated one, three, five and seven days after creation of the retinal detachment. For light microscopic analysis, the cornea and lens were removed and the remaining eyecup placed in a fixative containing 2.5% glutaraldehyde and 2% formaldehyde in 0.1M cacodylate buffer (pH 7.4) and stored at 4° C. overnight. Tissue samples then were post-fixed in 2% osmium tetroxide, dehydrated in graded ethanol, and embedded in epoxy resin. One-micron sections were stained with 0.5% toluidine blue in 0.1% borate buffer and examined with a Zeiss photomicroscope (Axiophot, Oberkochen, Germany).

At one day after creation of the detachment, pyknosis in the ONL was confined to the area of the peripheral retinotomy site through which the subretinal injector was introduced. By three days, however, pyknotic nuclei were seen in the whole ONL of the retina in the area of the detachment. Extrusion of pyknotic nuclei from the ONL into the subretinal space was observed. The remaining layers of the retina appeared morphologically normal. No inflammatory cells were seen, and there was no apparent disruption of the retinal vasculature. Similar changes were seen in sections from retinas detached for up to one week. No pyknotic nuclei were seen in the area of the attached retina or in the fellow, non-detached eye. The amount of ONL pyknosis was similar between detachments of three-day or one week duration.

Disruption of the photoreceptor outer segments was a prominent feature in the detached retinas. Outer segments of the control eyes and the attached portions of the experimental eyes had an orderly, parallel arrangement. Detachments produced artifactually during tissue processing in these eyes did not alter the photoreceptor morphology. In contrast, the photoreceptor outer segments of detached retinas were severely disorganized and lost their normal structural organization. Additionally, outer segments in attached areas had similar lengths, whereas the outer segments in detached areas showed variable lengths.

Internucleosomal DNA cleavage in photoreceptor cells was detected via TUNEL staining. For TUNEL staining, the cornea and lens were not removed after enucleation, but rather the whole eye was fixated overnight at 40° C. in a phosphate buffered saline solution of 4% paraformaldehyde solution (pH 7.4). Then, a section was removed from the superior aspect of the globe and the remaining eyecup embedded in paraffin and sectioned at a thickness of 6 μm. TUNEL staining was performed on these sections using the TdT-Fragel DNA Fragmentation Detection Kit (Oncogene Sciences, Boston, Mass.) in accordance with the manufacturer's instructions. Reaction signals were amplified using a preformed avidin: biotinylated-enzyme complex (ABC-kit, Vector Laboratories, Burlingame, Calif.). Internucleosomally cleaved DNA fragments were stained with diaminobenzidine (DAB) (staining indicates TUNEL-positive cells) and sections were then counterstained with methylene green.

TUNEL-positive cells were detected at all time points tested (one, three, five and seven days post-detachment). TUNEL-positive staining was confined only to the photoreceptor cell layer. Two eyes with retinal detachments that persisted for two months were monitored. The TUNEL assay at two months did not reveal any staining indicating the presence of internucleosomally cleaved DNA. The prolonged detachment was associated with a marked reduction in the thickness of and number of cell bodies contained in the ONL as compared to the non-detached retina.

Antibodies specific for caspases 3, 7, 9 and PARP were used in Western blots to probe total retinal protein extracts at various times after creation of the retinal detachment. For Western blot analysis, retinas from both experimental and control eyes were manually separated from the underlying retinal pigment epithelium/choroid at days one, three and five after creation of the retinal detachment. In eyes with retinal detachments, the experimentally detached portion of the retina was separated from the attached portion of the retina and analyzed separately. Retinas were homogenized and lysed with buffer containing 1 mM ethylene diaminetetraacetic acid/ethylene glycol-bis(2-aminoethylethel-N,N,N',N'-tetraacetic acid/dithiothreitol, 10 mM HEPES pH 7.6, 0.5% (octylphenoxy)polyethoxyethanol (IGEPAL), 42 mM potassium chloride, 5 mM magnesium chloride, 1 mM phenylmethanesulfonyl fluoride and 1 tablet of protease inhibitors per 10 ml buffer (Complete Mini, Roche Diagnostics GmbH, Mannheim, Germany). Samples were incubated for 15 minutes on ice, and then centrifuged at 21,000 rpm at 4° C. for 30 minutes. The protein concentration of the supernatant was determined using the Bio-Rad $D_C$ Protein Assay reagents (Bio-Rad Laboratories, Hercules, Calif.).

Proteins were separated via sodium dodecyl sulfate-polyacrylamide gel electrophoresis (7.5% and 15% Tris-HCL Ready-Gels, Bio-Rad Laboratories), in which 30 μg of total retinal protein were applied in each lane. The fractionated proteins were transferred to a PVDF membrane (Immobilon-P, Millipore, Bedford, Mass.). The resulting membrane was blocked with 5% non-fat dry milk in 0.1% TBST IGEPAL. The blocked membranes then were incubated with antibodies against caspase 7 (1:1,000; Cell Signaling Technology, Beverly, Mass.), caspase 9 (1:1,000; Medical & Biological Laboratories, Naka-ku Nagoya, Japan), cleaved-caspase 3 (1:1,000; Cell Signaling Technology, Beverly, Mass.), caspase 3 (1:2000; Santa Cruz, Santa Cruz, Calif.) or PARP (1:1000; Cell Signaling Technologies, Beverly, Mass.) overnight at 4° C. Bands were detected using the ECL-Plus reagent (Amersham, Pharmacia, Piscataway, N.J.). Membranes were exposed to HyperFilm (Amersham) and densitometry was preformed using ImageQuant 1.2 software (Molecular Dynamics, Inc., Sunnyvale, Calif.). For each eye tested, densitometry levels were normalized by calculating the ratio of the cleaved-form to the pro-form of the protein of interest. Pro-caspase 7 levels were normalized to the densitometry readings from a non-specific band detected by the secondary IgG. Five eyes were used for each time point, except for the PARP levels for day 5 after detachment for which only four eyes were used. All statistical comparisons were performed using a paired t-test.

The cleaved, or active form of caspase 3 was elevated in the detached retinas as compared to the attached retinas. The level of cleaved-caspase 3 increased as a function of time after detachment, with a peak at approximately three days (see, FIG. 1). No cleaved-caspase 3 was detected in the control eye or in the attached portion of the retina in the experimental eye.

Figure 2:
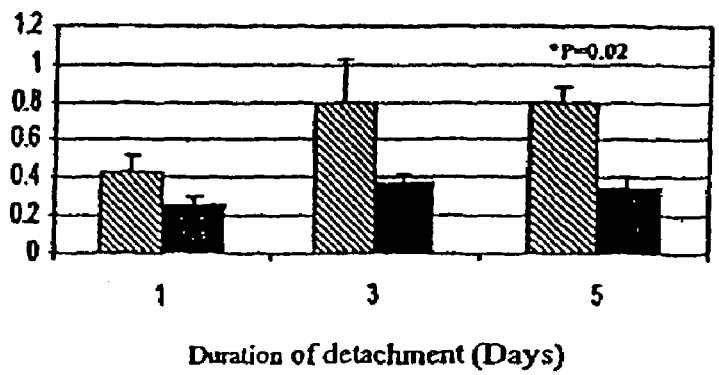
FIG. 2 depicts a bar chart showing the ratio of cleaved caspase 9 to pro-caspase 9 in densitometry units in detached retinas (hatched bars) and attached retinas (solid bars) at one, three and five days post retinal detachment.
Figure 3:
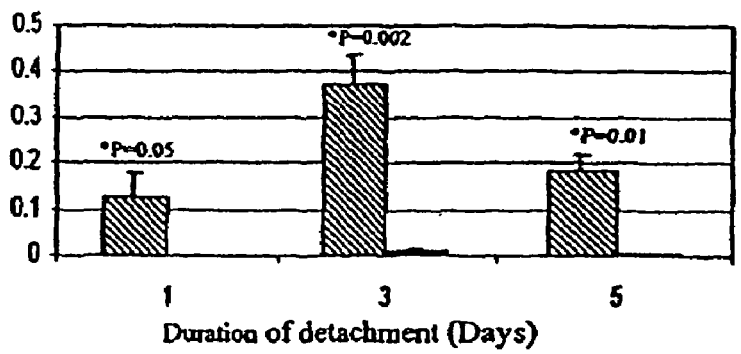
FIG. 3 depicts a bar chart showing the level of caspase 7 in densitometry units in detached retinas (hatched bars) and attached retinas (solid bars) at one, three and five days post retinal detachment.
Figure 4:
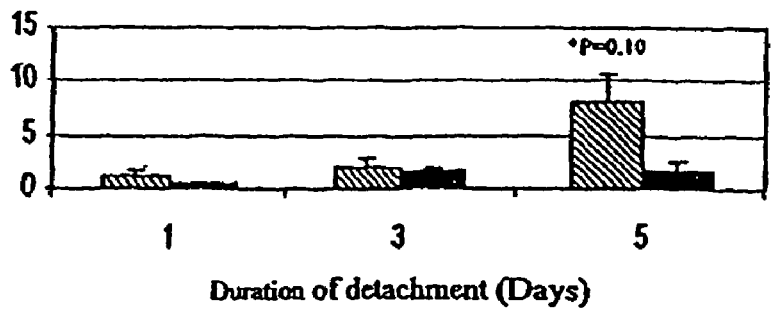
FIG. 4 depicts a bar chart showing the ratio of cleaved poly-ADP ribose-polymerase (PARP) to pro-PARP in densitometry units in detached retinas (hatched bars) and attached retinas (solid bars) at one, three and five days post retinal detachment.

The ratio of the active to inactive form of caspase 9 also increased as a function of time after creation of the experimental retinal detachment (see, FIG. 2). The peak level of cleaved-caspase 9 was seen at three to five days after creation of the detachment. The caspase 7 antibody was able only to detect the pro-form of the protein. There was, however, a significant difference in the amount of the pro-form detected in the protein extract from the detached retinas as compared to the attached retinas (see, FIG. 3). Western blotting with antibodies against PARP (a component of the apoptosis cascade downstream of caspase 7) detected an increase in the level of cleaved-PARP that was maximal at five days after detachment (see, FIG. 4). P-values for the comparisons between detached and attached retinas are shown in FIGS. 1-4.

The results demonstrate that caspase 3, caspase 7 and caspase 9 are all activated in photoreceptor cells following retinal attachment.

Example 2

Preservation of Photoreceptor Viability Following Retinal Detachment

The type of experiment provided herein may show that the viability of photoreceptor cells in a detached region of a retina can be maintained by administering a caspase inhibitor to an affected eye.

Retinal detachments are surgically induced in Brown-Norway rats as discussed in Example 1. The caspase inhibitor, Z-Val-Ala-Asp-fluoromethylketone is dissolved in dimethyl sulfoxide (DMSO) to give the final concentrations of 0.2 mM, 2 mM, and 20 mM. After creating the retinotomy with the subretinal injector, a small amount of Healon® sodium hyaluronate is injected in the subretinal space so as to elevate the retina. After retinal elevation, a Hamilton syringe with a 33 gauge needle is introduced through the retinotomy site, and 25 μl of inhibitor is injected into the region of detachment. About 25 minutes later, Healon® sodium hyaluronate is injected, via the same retinotomy site, to maintain the retinal detachment. Healon® sodium hyaluronate is injected until resistance is detected.

Only the right eyes of rats are used in evaluating the role of the Z-VAD-FMK inhibitor. The left eyes serve as the controls. Five animals are used for each concentration of inhibitor (namely, no inhibitor, 0.2 mM inhibitor, 2 mM inhibitor, and 20 mM inhibitor). For the no inhibitor control, 25 μl of DMSO is injected into the region of detachment followed by Healon® sodium hyaluronate.

After 72 hours, the eyes are enucleated and the rats euthanized. The enucleated eyes are paraffin embedded as described in Example 1. Then, 6 μm sections from the posterior segments are analyzed by TUNEL staining as described in Example 1. It is contemplated that there will be fewer photoreceptor cells in the region of retinal detachment that stain TUNEL-positive in eyes treated with the caspase inhibitor relative to eyes that have not been treated with the caspase inhibitor.

Example 3

Calcineurin is Cleaved During Retinal Detachment

This experiment provides evidence that in a retinal detachment animal model, calcineurin is cleaved to produce a constitutively active calcineurin molecule (i.e., lacking its autoinhibitory domain). This constitutively active molecule has its active site exposed, but, because it lacks the autoihibitory domain, the active site cannot be hidden. Thus, this cleaved form of calcineurin can activate the apoptotic pathway in photoreceptor cells.

All experiments were performed in accordance with the ARVO Statement for the Use of Animals in Ophthalmic and Vision Research and the guidelines established by the Animal Care Committee of the Massachusetts Eye and Ear Infirmary. Adult male Brown Norway rats (300-450 g, Charles River, Boston, Mass.) were used in this study, and retinal detachments were created as previously described (Zacks et al. (2003) INVEST. OPHTHALMOL. VIS. SCI. 44(3):1262-7). Rats were anesthetized using a mixture of ketamine (100 mg/ml) and xylazine (20 mg/ml). Pupilary dilation was performed using topical phenylephrine (5.0%)/tropicamide (0.8%). A sclerotomy was created approximately 2 mm posterior to the limbus with a 20 gauge micro-vitreoretinal blade (MVR, Becton-Dickinson, Franklin Lakes, N.J.), and care was taken to avoid damage to the lens during the creation of the sclerotomy. A Glaser subretinal injector (20 gauge shaft with a 32 gauge tip, Becton-Dickinson, Franklin Lakes, N.J.) connected to a syringe filled with 10 mg/ml of Healon® sodium hyaluronate (Pharmacia and Upjohn Company, Kalamazoo, Mich.) was introduced into the vitreous cavity. In the peripheral retina, a retinotomy was created using the tip of the subretinal injector. Healon was injected slowly into the subretinal space, elevating the retina from the underlying RPE. Retinal detachments was only created in one eye of each animal, with the fellow eye serving as the control. After harvesting the eye, the proteins were collected, run out on a gel, and detected using western blotting (as described more fully in Example 4).

Figure 5:
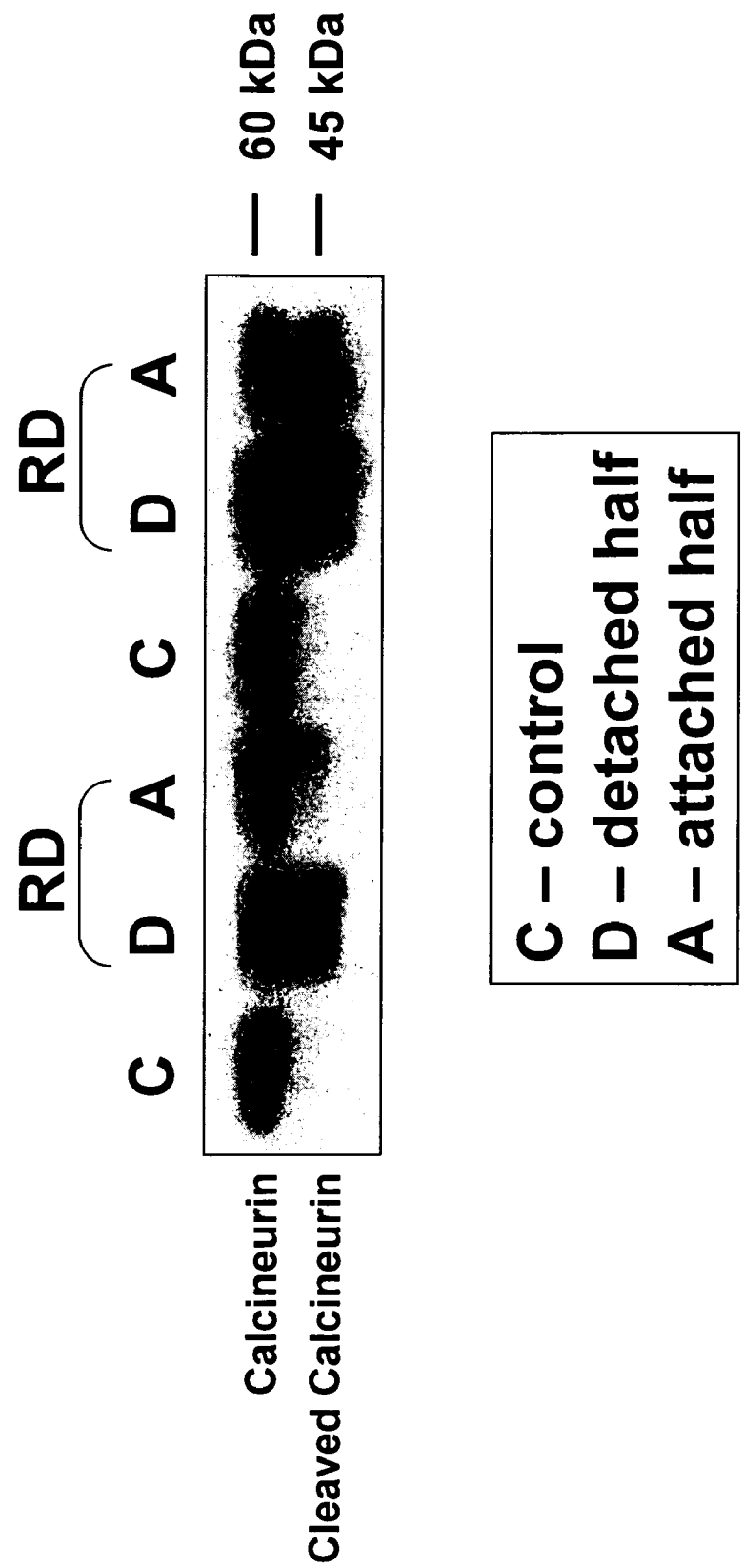
FIG. 5 depicts a gel displaying the pattern of calcineurin cleavage into its constitutively active form in detached retinas.

FIG. 5 shows a gel indicating that the 45 kDa cleaved calcineurin (i.e., constitutively active calcineurin) is present in the detached portion of a retina at a higher level than the attached portion of the retina. This indicates that calcineurin, particularly constitutively active calcineurin, and cell death, are intertwined in retinal detachment.

Example 4

Modulation of the Calcineurin Pathway and Preservation of Photoreceptor Cells

Figure 6:
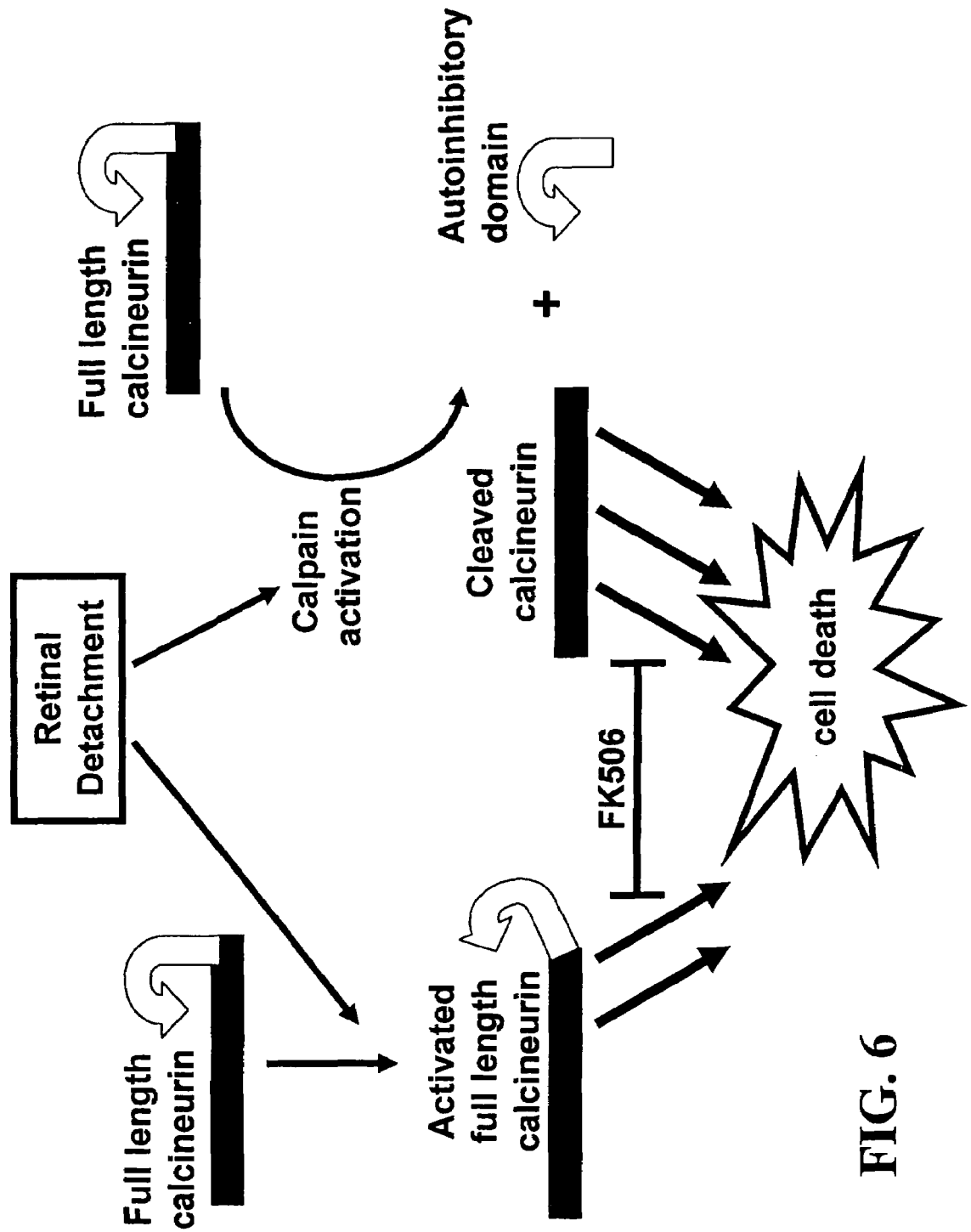
FIG. 6 depicts two schematic pathways of calcineurin-mediated cell death following retinal detachment, one involving activated, full length, native calcineurin and one involving truncated, constitutively active calcineurin. FK506 can inhibit both pathways.
Figure 7A:
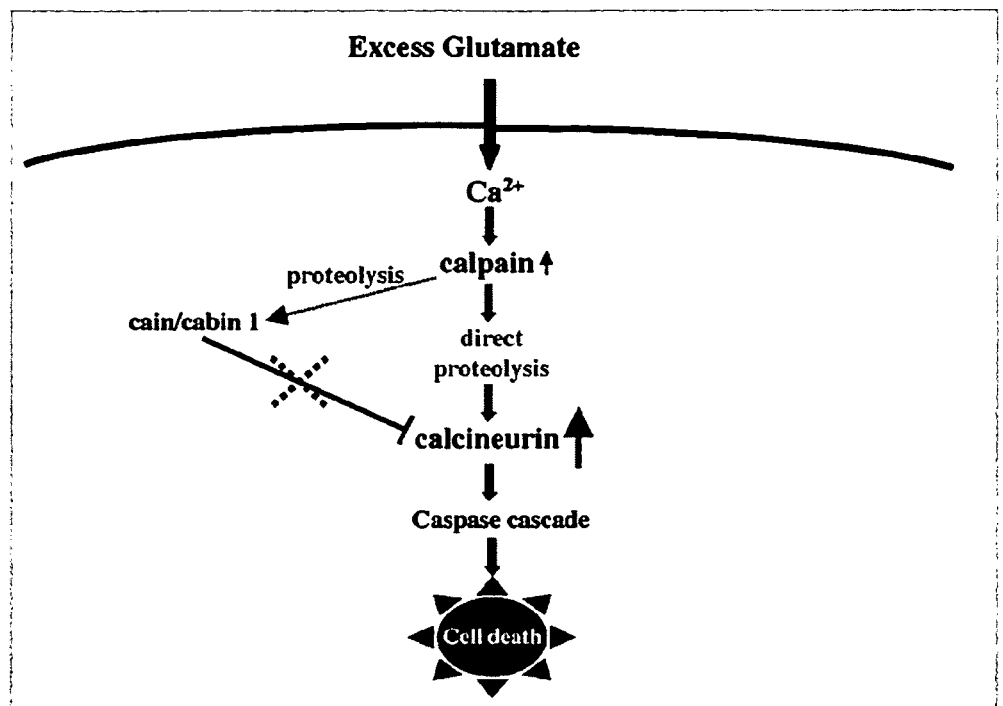
FIG. 7A depicts a schematic pathway of $Ca^{++}$/calmodulin-independent regulation of calcineurin activity during excessive glutamate-induced neuronal apoptosis and FIG. 7B depicts a schematic pathway of calpain-mediated activation of calcineurin, in which CaN B represents a calcineurin B-binding domain, CaN indicates calcineurin, and CaM represents calmodulin or its binding domain.
Figure 7B:
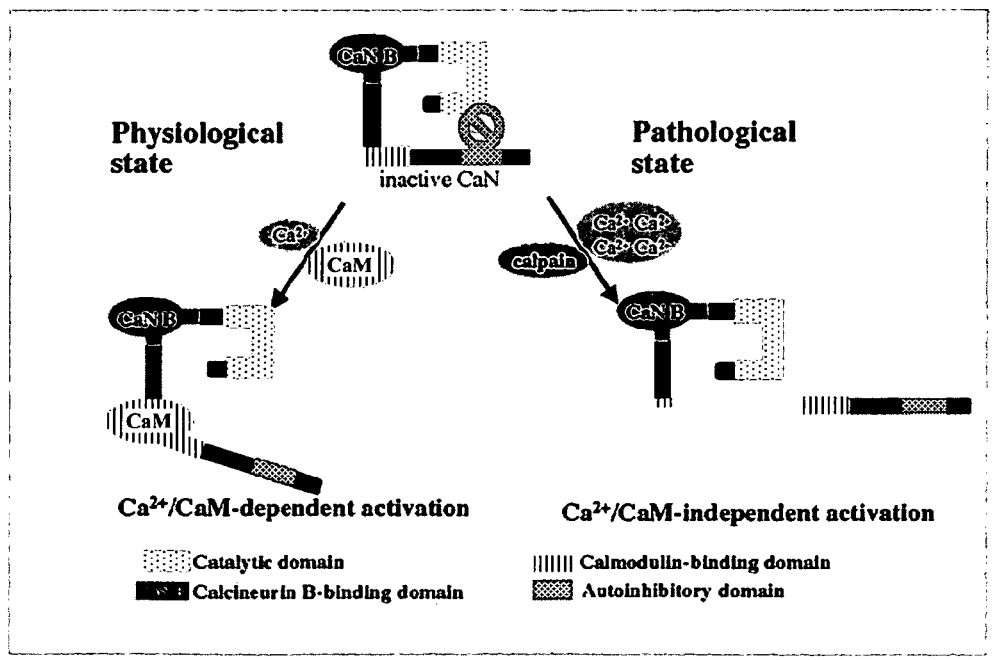

Calcineurin is an intracellular enzyme known to be activated by increases in intracellular calcium and thought to be involved in neuronal cell death. It was previously shown that inhibition of calcineurin by oral administration of the drug FK506 is neuroprotective in a rat model of experimental optic nerve injury (Freeman et al. (2000) INVEST. OPHTALMOL. VIS. SCI. 41(b):1111-5) and in experimental glaucoma (Huang et al. (2005) PNAS U.S.A. 102(34):12242-7). Recently, calcineurin has been shown to be cleaved, losing its autoinhibitory domain, following increases in intracellular calcium in neurons (Wu et al. (2004) J. BIOL. CHEM. 279(6):4929-40). It is contemplated that this cleavage occurs in photoreceptor cells in experimental retinal detachment and that it is mediated by calpain. It is also contemplated that inhibition of calpain will diminish the cleavage of calcineurin and that this inhibition will protect photoreceptor cells. As well, it is contemplated that inhibition of calcineurin in its native form as well as in it constitutively active form will protect photoreceptor cells. FIG. 6 depicts both the native calcineurin pathway that is blocked by FK506 as well as the cleaved calcineurin pathway that can be blocked by both FK506 and calpain inhibitors. More detail of these two pathways are provided in FIG. 7B and FIG. 7A, which are adapted from Wu et al. (2004) J. BIOL. CHEM. 279: 4929-4940.

The following experiments determine that calcineurin is cleaved after retinal detachment and that pharmacologic inhibition of calpain will prevent this activation. In particular, retinas of rats with experimental retinal detachment will be examined for biochemical evidence of calcineurin activation. These experiments also determine that calcineurin cleavage is mediated by the calcium-dependent enzyme, calpain. Experimentally, this is done by treating the rats with a calpain inhibitor, ALLM, and it is contemplated that this treatment will inhibit the cleavage of calcineurin in the retinal detachment model and protect photoreceptor cells from death in experimental retinal detachment. Finally, they determine that calcineurin inhibitors like FK506 have a neuroprotective effect on photoreceptor cells death.

Experiment #1

This experiment shows that calcineurin is cleaved in experimental retinal detachment. To show this result, retinal detachment is induced in rats by the method of Zacks et al. (2003) INVEST. OPHTHALMOL. VIS. SCI. 44(3): 1262-7, and as described below. Three or five days after retinal detachment, animals are sacrificed, and the retinas are removed for isolation of retinal protein or immunohistochemistry. Fellow eyes serve as controls. Western blot analysis is used to determine levels of retinal calcineurin as well as calcineurin cleavage products. Based on prior experience, 6 animals are needed in each group for each time point. It is contemplated that calcineurin will be shown to be cleaved.

Experiment #2

This experiment shows that calcineurin cleavage in experimental retinal detachment is mediated by calpain. To show this result, retinal detachment is induced in rats by the same method. One day prior to surgical induction, animals are started on a treatment of ALLM (20 mg/kg/day, intraperitoneal administration), a calpain inhibitor, or vehicle control, and administration continues throughout the study. For this experiment, the animals are followed for three or five days after retinal detachment. At the end of this period, animals are sacrificed and their eyes are removed for either protein isolation or immunohistochemistry. Fellow eyes are used as controls. Western blot analysis is used to determine levels of retinal calcineurin and calcineurin cleavage products. Six animals per group are used. It is contemplated that these levels will reflect inhibition of the calpain-mediated cleavage pathway by ALLM.

Experiment #3

This experiment demonstrates that inhibition of calcineurin protects photoreceptors cells in experimental retinal detachment. Rats begin treatment with FK506 or vehicle control. The following day, experimental retinal detachment is surgically induced in one eye of each animal. The fellow eye serves as a control. After three days, animals are sacrificed and their eyes removed for the counting of apoptotic photoreceptor cells. The total number of TUNEL-positive cells are counted in each eye, and the number of TUNEL-positive cells in the eyes of animals receiving FK506 are compared with the total number of TUNEL-positive photoreceptor cells in animals receiving vehicle control alone. It is contemplated that animals in which calcineurin is inhibited with FK506 will have fewer apoptotic photoreceptor cells than in animals receiving vehicle control. Ten animals in each group are used. With two groups, a total of 20 animals are used.

It is contemplated that these experiments will confirm that calpain-mediated cleavage of calcineurin occurs during retinal detachment and contributes to photoreceptor cell death. Insofar as both of activation of calcineurin and cleavage of calcineurin to its constitutively active form may be occurring, treatment with FK506 will inhibit calcineurin though one or both of these mechanisms, leading to a reduction in photoreceptor cell death. The specific methods for each of these experiments follow.

Retinal Detachment Model. All experiments mentioned above are performed in accordance with the ARVO Statement for the Use of Animals in Ophthalmic and Vision Research and the guidelines established by the Animal Care Committee of the Massachusetts Eye and Ear Infirmary. Adult male Brown Norway rats (300-450 g, Charles River, Boston, Mass.) are used in the studies, and retinal detachments are created as previously described (Zacks et al. (2003) INVEST. OPHTHALMOL. VIS. SCI. 44(3):1262-7. Rats are anesthetized using a mixture of ketamine (100 mg/ml) and xylazine (20 mg/ml). Pupilary dilation is performed using topical phenylephrine (5.0%)/tropicamide (0.8%). A sclerotomy is created approximately 2 mm posterior to the limbus with a 20 gauge micro-vitreoretinal blade (MVR, Becton-Dickinson, Franklin Lakes, N.J.). Care is taken to avoid damage to the lens during creation of the sclerotomy. A Glaser subretinal injector (20 gauge shaft with a 32 gauge tip, Becton-Dickinson, Franklin Lakes, N.J.) connected to a syringe filled with 10 mg/ml of Healon® sodium hyaluronate (Pharmacia and Upjohn Company, Kalamazoo, Mich.) is introduced into the vitreous cavity. In the peripheral retina, a retinotomy is created using the tip of the subretinal injector. Healon is injected slowly into the subretinal space, elevating the retina from the underlying RPE. Retinal detachments are only be created in one eye of each animal, with the fellow eye serving as the control.

Drug administration. FK506 (5 mg/kg/day) is administered by gavage in conscious animals beginning one day prior to induction of experimental retinal detachment.

Histologic analysis. At the termination of each experiment, animals are killed with an overdose of anesthesia and an intracardiac perfusion performed. Eyes are then be removed and fixed briefly in 4% paraformaldehyde. Eyes are prepared by immersion in graded sucrose solutions for cryoprotection and then embedded in OCT for cryostat sectioning. Immunohistochemistry and TUNEL staining are performed on cryostat sections using commercially available antibodies to calcineurin.

Western blot analysis. Animals are killed with an overdose of anesthesia and an intracardiac perfusion performed with phosphate buffered saline. Eyes are enucleated, and the retinas are then removed and retinal cell lysates prepared. Retinal cell lysate protein is then subjected to polyacrylamide gel electrophoresis, transferred to the appropriate membrane, probed for the presence of calcineurin proteins and cleavage products with appropriate antibodies, and visualized by chemiluminescence.

Example 5

Effect of Systemic Administration of FK506 in a Rat Model of Retinal Detachment

This example demonstrates the action of FK506 on photoreceptor apoptosis in a rat model of retinal detachment. As initially mentioned in Example 4, Experiment #3, this example demonstrates that inhibition of calcineurin protects photoreceptor cells in retinal detachment. This protection likely occurs through one or both of two pathways: activation of calcineurin and cleavage of calcineurin to its constitutively active form.

Methods. Retinal detachments were created in the eyes of Brown Norway rats by injecting 10% hyaluronic acid into the subretinal space using a transvitreal approach. FK506 (tacrolimus) (5 mg/kg/day) diluted in PBS was administered by gastric gavage one day prior to the induction of retinal detachment, on the day of the induction, and for the two following days (n=6). Control animals received the same volume of PBS (0.5 cc) by gastric gavage one day prior to the induction of retinal detachment, on the day of the induction, and for the two following days (n=3). Additional controls included animals that did not undergo retinal detachment and either were treated with FK506 (n=2) or received PBS (n=2). All eyes were enucleated 72 hours after retinal detachment induction and embedded in paraffin. Fourteen micrometer sections were subsequently obtained. DNA fragmentation was examined using terminal dUTP-biotin nick end-labeling (TUNEL). A masked observer counted TUNEL-positive cells and obtained an average from three adjacent standardized fields in two serial sections.

Results. Pyknotic nuclei in the outer nuclear layer (ONL) and disruption of the outer segments were noted in the area of the detachment. TUNEL-positive cells were present in the ONL only in the areas of retinal detachment. Animals treated with FK506 were noted to have fewer TUNEL-positive cells compared to the eyes of control animals: 130.13±54.3 vs. 195.5±25.04 (mean±SD). There was a 35% reduction in the mean number of TUNEL-positive cells in the treated group ($p<0.05$, Student's one-tailed t-test).

Discussion. Eyes that did not undergo retinal detachment showed normal morphology whether or not the animal received FK506, and no morphological signs of toxicity were noted in the eyes of treated animals. Animals treated with the calcineurin inhibitor showed fewer apoptotic photoreceptor cells in the ONL layer following detachment, as compared to animals receiving vehicle control. These data suggest that systemic administration of the therapeutic agent FK506 may inhibit photoreceptor apoptosis associated with retinal detachment. Without being bound by theory, it is believed that insofar as both activation of calcineurin and cleavage of calcineurin to its constitutively active form may be occurring in retinal detachment, treatment with calcineurin inhibitors, such as FK506, inhibits calcineurin through one or both of these mechanisms, leading to a reduction in photoreceptor cell death.

INCORPORATION BY REFERENCE

The entire content of each patent and non-patent document disclosed herein is expressly incorporated herein by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of preserving the viability of photoreceptor cells disposed within a retina of a mammalian eye following retinal detachment, the method comprising:

administering to a mammal having an eye in which a region of the mammal's own retina has been detached an amount of FK506 sufficient to preserve the viability of photoreceptor cells disposed within the region of the mammal's own detached retina;

wherein the FK506 is administered to the mammal prior to or during reattachment of the region of the mammal's own detached retina.

2. The method of claim 1, wherein the FK506 is administered to the mammal prior to reattachment of the region of detached retina.

3. The method according to claim 1, wherein the FK506 is administered to the mammal during reattachment of the region of detached retina.

4. The method of claim 1, wherein the FK506 is administered locally or systemically.

5. The method of claim 1, wherein the FK506 is administered by intraocular, intravitreal, or transcleral administration.

6. The method of claim 1, wherein the FK506 reduces the number of photoreceptor cells in the region that die following retinal detachment.

7. The method of claim 1, wherein the retinal detachment occurs as a result of a retinal tear, retinoblastoma, melanoma, diabetic retinopathy, uveitis, choroidal neovascularization, retinal ischemia, pathologic myopia, hemorrhage, or trauma.

* * * * *

SEQUENCE LISTING

<160> NUMBER OF SEQ ID NOS: 6

<210> SEQ ID NO 1
<211> LENGTH: 19
<212> TYPE: PRT
<213> ORGANISM: Artificial Sequence
<220> FEATURE:
<223> OTHER INFORMATION: Caspase 1 inhibitor
<220> FEATURE:
<221> NAME/KEY: misc_feature

```
<222> LOCATION: (1)..(1)
<223> OTHER INFORMATION: X is Ac-Ala.
<220> FEATURE:
<221> NAME/KEY: misc_feature
<222> LOCATION: (19)..(19)
<223> OTHER INFORMATION: X is Asp-aldehyde.

<400> SEQUENCE: 1

Xaa Ala Val Ala Leu Leu Pro Ala Val Leu Leu Ala Leu Leu Pro Tyr
1               5                   10                  15

Val Ala Xaa

<210> SEQ ID NO 2
<211> LENGTH: 20
<212> TYPE: PRT
<213> ORGANISM: Artificial Sequence
<220> FEATURE:
<223> OTHER INFORMATION: Caspase 3 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 2

Xaa Ala Val Ala Leu Leu Pro Ala Val Leu Leu Ala Leu Leu Ala Pro
1               5                   10                  15

Asp Glu Val Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Caspase 4 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Pro-aldehyde.

<400> SEQUENCE: 3

Xaa Ala Val Ala Leu Leu Pro Ala Val Leu Leu Ala Leu Leu Ala Pro
1               5                   10                  15

Leu Glu Val Xaa
            20

<210> SEQ ID NO 4
<211> LENGTH: 20
<212> TYPE: PRT
<213> ORGANISM: Artificial Sequence
<220> FEATURE:
<223> OTHER INFORMATION: Caspase 6 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 4
```

```
Xaa Ala Val Ala Leu Leu Pro Ala Val Leu Leu Ala Leu Leu Ala Pro
1               5                   10                  15

Val Glu Ile Xaa
            20

<210> SEQ ID NO 5
<211> LENGTH: 20
<212> TYPE: PRT
<213> ORGANISM: Artificial Sequence
<220> FEATURE:
<223> OTHER INFORMATION: Caspase 8 inhibitor
<220> FEATURE:
<221> NAME/KEY: misc_feature
<222> LOCATION: (1)..(1)
<223> OTHER INFORMATION: X is AC-ALA
<220> FEATURE:
<221> NAME/KEY: misc_feature
<222> LOCATION: (20)..(20)
<223> OTHER INFORMATION: X is Asp-aldehyde.

<400> SEQUENCE: 5

Xaa Ala Val Ala Leu Leu Pro Ala Val Leu Leu Ala Leu Leu Ala Pro
1               5                   10                  15

Ile Glu Tyr Xaa
            20

<210> SEQ ID NO 6
<211> LENGTH: 20
<212> TYPE: PRT
<213> ORGANISM: Artificial Sequence
<220> FEATURE:
<223> OTHER INFORMATION: Caspase 9 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 6

Xaa Ala Val Ala Leu Leu Pro Ala Val Leu Leu Ala Leu Leu Ala Pro
1               5                   10                  15

Leu Glu His Xaa
            20
```